US007235715B2

(12) United States Patent
Tumer et al.

(10) Patent No.: US 7,235,715 B2
(45) Date of Patent: Jun. 26, 2007

(54) VIRUS-RESISTANT TRANSGENIC PLANTS EXPRESSING L3

(75) Inventors: Nilgun E. Tumer, Belle Mead, NJ (US); Jonathan D. Dinman, North Brunswick, NJ (US); Katalin A. Hudak, East Brunswick, NJ (US)

(73) Assignees: Rutgers, The State University, New Brunswick, NJ (US); The University of Medicine and Dentistry of New Jersey, New Brunswick, NJ (US)

( * ) Notice: Subject to any disclaimer, the term of this patent is extended or adjusted under 35 U.S.C. 154(b) by 535 days.

(21) Appl. No.: 10/636,386

(22) Filed: Aug. 7, 2003

(65) Prior Publication Data

US 2005/0114927 A1 May 26, 2005

Related U.S. Application Data

(63) Continuation of application No. 09/869,176, filed as application No. PCT/US99/31312 on Dec. 30, 1999, now abandoned.

(60) Provisional application No. 60/115,791, filed on Dec. 31, 1998.

(51) Int. Cl.

| | |
|---|---|
| *C12N 15/82* | (2006.01) |
| *C12N 5/04* | (2006.01) |
| *C12N 1/20* | (2006.01) |
| *C12N 15/81* | (2006.01) |
| *C12N 15/70* | (2006.01) |
| *C07H 21/04* | (2006.01) |
| *A01H 5/10* | (2006.01) |

(52) U.S. Cl. ............ 800/301; 435/252.33; 435/254.21; 435/419; 435/468; 536/23.74; 800/279; 800/288

(58) Field of Classification Search ..................... None
See application file for complete search history.

(56) References Cited

U.S. PATENT DOCUMENTS 5,196,510 A 3/1993 Rodwell et al.
5,248,606 A 9/1993 Walsh et al.
5,646,026 A 7/1997 Walsh et al.
5,756,322 A 5/1998 Tumer
6,060,646 A 5/2000 Harris et al.

OTHER PUBLICATIONS

Mitterbauer et al., Plant Biotech. J., 2004, vol. 2, pp. 329-340.*
Linthorst et al., The Plant Cell, (1):285-291 (1989).
Kim et al., Gene, (93):177-182 (1990).
Schultz et al., Journal of Bacteriology. Jul. 1983, 155-1:8 14, especially pp. 8, 9 and 11.
Lodge et al., Proc. Natl. Acad. Sci., USA, 1993, vol. 90, pp. 7089-7093.
Sambrook et al.; Molecular Cloning A Laboratory Manual, Second Ed., 1989, Cold Spring Harbor Press, pp. 1.74-1.84.
Peltz et al., Molecular and Cellular Biology, vol. 19, No. 1, pp. 384-391 (1999).
Fried et al., Proc. Natl. Acad. Sci. USA, vol. 78, No. 1, pp. 238-242 (1981).

* cited by examiner

*Primary Examiner*—Ashwin Mehta
(74) *Attorney, Agent, or Firm*—Lerner, David, Littenberg, Krumholz & Mentlik, LLP

(57) ABSTRACT

Disclosed are transgenic plants containing an exogenous nucleic acid encoding an L3 protein. The plant exhibits increased resistance to viruses and/or fungi that infect plants. The L3 proteins include wild-type proteins, spontaneously occurring mutants and non-naturally occurring L3 mutants. Also disclosed are methods of reducing the toxicity of single-chain ribosome inhibitory proteins in cells, e.g., yeast, plant and animal cells, by co-administering the L3 protein with the RIP. Further disclosed are non-naturally occurring L3 mutants that (a) substantially fail to bind single-chain RIPs that bind endogenous L3 proteins, (b) are unable to maintain M1 killer virus, (c) promote altered programmed ribosomal frameshift efficiency, (d) exhibit resistance to peptidyltransferase inhibitors, and combinations of any of (a)–(d).

22 Claims, No Drawings

VIRUS-RESISTANT TRANSGENIC PLANTS EXPRESSING L3

CROSS-REFERENCE TO RELATED APPLICATIONS

This application is a continuation of U.S. application Ser. No. 09/869,176, filed Jun. 26, 2001, now abandoned which is a National Phase entry of PCT/US99/31312, filed Dec. 30, 1999, which claims priority under 35 U.S.C §119(e) from U.S. application No. 60/115,791, filed Dec. 31, 1998, the content of which is incorporated by reference.

STATEMENT REGARDING FEDERALLY SPONSORED RESEARCH

The development of this invention was supported in part by National Science Foundation Grants MCB96-31308, MCB97-27941 and MCB98-07890. Therefore, the Government may have certain rights in the invention.

BACKGROUND OF THE INVENTION

This invention relates generally to agricultural biotechnology, and more specifically to methods and genetic elements for conferring resistance to fungi and/or viruses in plants.

The subject of plant protection against pathogens remains the area of utmost importance in agriculture. Many commercially valuable agricultural crops are prone to infection by plant viruses and fungi capable of inflicting significant damage to a crop in a given season, and drastically reducing its economic value. The reduction in economic value to the farmer in turn results in a higher cost of goods to ultimate purchasers. Several published studies have been directed to the expression of plant virus capsid proteins in a plant in an effort to confer resistance to viruses. See, e.g. Abel, et al., Science 232:738–743 (1986); Cuozzo, et al., Bio/Technology 6:549–57 (1988); Hemenway, et al., EMBO J. 7:1273–80 (1988); Stark, et al., Bio/Technology 7:1257–62 (1989); and Lawson, et al., Bio/Technology 8:127–34 (1990). However, the transgenic plants exhibited resistance only to the homologous virus and related viruses, but not to unrelated viruses. Kawchuk, et al., Mol. Plant-Microbe Interactions 3(5):301–307 (1990), disclose the expression of wild-type potato leafroll virus (PLRV) coat protein gene in potato plants. Even though the infected plants exhibited resistance to PLRV, all of the transgenic plants that were inoculated with PLRV became infected with the virus and thus disadvantageously allowed for the continued transmission of the virus such that high levels of resistance could not be expected. See U.S. Pat. No. 5,304,730.

Fungal pathogens contribute significantly to the most severe pathogen outbreaks in plants. Plants have developed a natural defense system, including morphological modifications in their cell walls, and synthesis of various anti-pathogenic compounds. See, e.g. Boller, et al., Plant Physiol. 74:442–444 (1984); Bowles, Annu. Rev. Biochem. 59:873–907 (1990); Joosten, et al., Plant Physiol. 89:945–951 (1989); Legrand, et al., Proc. Natl. Acad. Sci. USA 84:6750–6754 (1987); and Roby, et al., Plant Cell 2:999–1007 (1990). Several pathogenesis-related (PR) proteins have been shown to have anti-fungal properties and are induced following pathogen infection. These are different forms of hydrolytic enzymes, such as chitinases and β-1,3-glucanases that inhibit fungal growth in vitro by destroying fungal cell walls. See, e.g. Boller, et al., supra; Grenier, et al., Plant Physiol. 103:1277–123 (1993); Leah, et al., J. Biol. Chem. 266:1464–1573 (1991); Mauch, et al., Plant Physiol. 87:325–333 (1988); and Sela-Buurlage Buurlage, et al., Plant Physiol. 101:857–863 (1993).

Several attempts have been made to enhance the pathogen resistance of plants via recombinant methodologies using genes encoding pathogenesis-related proteins (such as chitinases and β-1,3-glucanases) with distinct lytic activities against fungal cell walls. See, e.g., Broglie, et al., Science 254:1194–1197 (1991); Vierheilig, et al., Mol. Plant-Microbe Interact. 6:261–264 (1993); and Zhu, et al., Bio/Technology 12:807–812 (1994). Recently, two other classes of genes have been shown to have potential in conferring disease resistance in plants. Wu, et al., Plant Cell 7:1357–1368 (1995), reports that a transgenic potato expressing the *Aspergillus niger* glucose oxidase gene exhibited increased resistance to *Erwinia carotovora* and *Phytophthora infestans*. The hypothesis is that the glucose oxidase-catalyzed oxidation of glucose produces hydrogen peroxide, which when accumulates in plant tissues, leads to the accumulation of active oxygen species, which in turn, triggers production of various anti-pathogen and anti-fungal mechanisms such as phytoalexins (see Apostol, et al., Plant Physiol. 90:109–116 (1989) and Degousee, Plant Physiol. 104:945–952 (1994)), pathogenesis-related proteins (Klessig, et al., Plant Mol. Biol. 26:1439–1458 (1994)), strengthening of the plant cell wall (Brisson, et al., Plant Cell 6:1703–1712 (1994)), induction of systemic acquired resistance by salicylic acid (Chen, et al., Science 162:1883–1886 (1993)), and hypersensitive defense response (Levine, et al., Cell 79:583–593 (1994)).

In addition to the studies on virus resistance in plants, ribosome inactivating proteins (RIPs) have been studied in conjunction with fungal resistance. For example, Logeman, et al., Bio/Technology 10:305–308 (1992), report that an RIP isolated from barley endosperm provided protection against fungal infection to transgenic tobacco plants. The combination of barley endosperm RIP and barley class-II chitinase has provided synergistic enhancement of resistance to *Rhizoctonia solani* in tobacco, both in vitro and in vivo. See, e.g., Lea, et al., supra; Mauch, et al., supra; Zhu, et al., supra; and Jach, et al., The Plant Journal 8:97–109 (1995). PAP, however, has not shown antifungal activity in vitro. See Chen, et al., Plant Pathol. 40:612–620 (1991), which reports that PAP has no effect on the growth of the fungi *Phytophthora infestans, Colletotrichum coccodes, fusarium solani, fusarium sulphureum, Phoma foreata* and *Rhizoctonia solani* in vitro.

Lodge, et al., Proc. Natl. Acad. Sci. USA 90:7089–7093 (1993), report the *Agrobacterium tumefaciens*-mediated transformation of tobacco with a cDNA encoding wild-type pokeweed antiviral protein (PAP) and the resistance of the transgenic tobacco plants to unrelated viruses. PAP, a Type I ribosome-inhibiting protein (RIP) found in the cell walls of *Phytolacca americana* (pokeweed), is a single polypeptide chain that catalytically removes a specific adenine residue from a highly conserved stem-loop structure in the 28S rRNA of eukaryotic ribosomes, and interferes with elongation factor-2 binding and blocking cellular protein synthesis. See, e.g., Irvin et al., Pharmac. Ther. 55:279–302 (1992); Endo, et al., Biophys. Res. Comm., 150:1032–1036 (1988); and Hartley, et al., FEBS Lett. 290:65–68 (1991). The observations by Lodge were in sharp contrast to previous studies, supra, which reported that transgenic plants expressing a viral gene were resistant to that virus and closely related viruses only. See also Beachy, et al., Ann. Rev. Phytopathol. 28:451–474 (1990); and Golemboski, et al., Proc. Natl. Acad. Sci. USA 87:6311–15 (1990). Lodge also reports, however, that the PAP-expressing tobacco plants (i.e., above 10 ng/mg protein) tended to have a stunted, mottled phenotype, and that other transgenic tobacco plants that accumulated the highest levels of PAP were sterile. RIPs have proven unpredictable in other respects such as target specificity. Unlike PAP which (as demonstrated in Lodge, supra), ricin isolated from castor bean seed is 1000 times more active on mammalian ribosomes than plant ribosomes. See, e.g., Harley, et al., Proc. Natl. Acad. Sci. USA 79:5935–5938 (1982). Barley endosperm RIP also shows very little activity against plant ribosomes. See, e.g. Endo, et al., Biochem. Biophys. Acta 994:224–226 (1988) and Taylor, et al., Plant J. 5:827–835 (1984).

U.S. Pat. Nos. 5,756,322 and 5,880,322 teach PAP mutants that when produced in plants exhibit less toxicity than wild-type PAP and exhibit biological activities (e.g., resistance to viruses, fungi and other pests) akin to wild-type PAP. It has also been reported that PAP II and PAP II mutants exhibit reduced phytotoxicity compared to wild-type PAP. See Wang, et al., Plant Mol. Biol. 38:957–964 (1998).

Nonetheless, a need remains for a means by which to confer broad spectrum virus and/or fungus resistance to plants without causing cell death or sterility, and which requires a minimum number of transgenes. There is also a need to enhance the anti-viral and anti-fungal properties imparted by PAP while reducing the phytotoxicity associated with PAP.

SUMMARY OF THE INVENTION

L3 is a highly conserved ribosomal protein that participates in the formation of the peptidyltransferase center that in turn allows elongation of the ribosome along the messenger RNA (mRNA). Hampl, et al., J. Biol. Chem. 256: 2284–2288 (1981); Noller, J. Bacteriol. 175:5297–5300 (1993). L3 also plays an essential role in the catalysis of peptide bond formation. See, Green, et al., Annu. Rev. Biochem. 66:679–716 (1997). This is an essential step in protein synthesis in yeast, animals and higher plants.

Applicants have discovered that PAP, a protein that imparts resistance to plant pests such as viruses and fungi when expressed in or applied to plants but which is relatively toxic to plants, recognizes its ribosomal substrate by binding to L3. Applicants have also discovered that PAP does not depurinate ribosomes and thus is non-toxic in the presence of certain L3 mutants. Applicants have further discovered that expression of L3 proteins in plants confers resistance to a broad range of viruses and fungi.

Accordingly, a first aspect of the present invention is directed to a transgenic plant having an exogenous nucleic acid containing a sequence encoding an L3 protein. Expression of the L3 nucleic acid sequence results in increased resistance to a broad spectrum of viruses and fungi to the plant. In preferred embodiments, the L3 nucleic acid is obtained or derived from yeast, a higher plant or an animal. It may be homologous or heterologous with respect to the plant in which it is being introduced. In other preferred embodiments, the L3 protein is a spontaneously occurring mutant of L3 or a non-naturally occurring L3 mutant. In other preferred embodiments, the transgenic plant also has a second exogenous nucleic acid containing a sequence encoding a single chain RIP that acesses ribosomes (and depurinates them) by binding an endogenous L3 protein, the expression of which results in increased anti-fungal and/or anti-fungal resistance to the plant. In more preferred embodiments, the RIP is PAP, a PAP mutant, PAP-v, PAP II or a PAP II mutant. Preferred transgenic plants include monocots and dicots. Protoplasts and plant cells transformed (stably or transiently) with exogenous nucleic acid(s) are also provided. Seed derived from the transgenic plants are further provided. An advantage of using L3 is that unlike PAP and other RIPs, it is substantially non-toxic to both prokaryotic and eukaryotic cells and whole plants.

Another aspect of the present invention is directed to methods of increasing resistance to viruses and fungi in plants by administering to a plant the L3 proteins of the present invention In one preferred embodiment, the L3 nucleic acid is introduced into the plant; in another, it is introduced into a protoplast and the whole plant is regenerated therefrom.

Yet another aspect of the present invention is directed to methods for reducing the phytotoxicity associated with the production in plants of anti-viral and/or anti-fungal single-chain RIPs such as PAP, PAP-v and PAP II proteins. The methods entail co-production of an L3 protein. Without intending to be bound by any particular theory of operation, Applicants believe that expression of exogenous wild type L3 competes with the RIP for binding to the endogenous L3 protein and thus reduces phytotoxicity. It is also believed that the L3 mutants of the present invention do not bind the RIP thus severing the pathway that leads to the phytotoxic effect but still allow for an anti-viral and/or anti-fungal phenotype.

A further aspect of the present invention is directed to nucleic acids that encode various non-naturally occurring L3 mutants. The mutants are characterized by one or more of the following properties, namely: they substantially fail to bind single-chain RIPs that bind endogenous L3 to access ribosomes in vivo; they are unable to maintain an M1 killer virus; they alter (e.g. increase or in some cases, decrease) programmed ribosomal frameshift efficiency and they exhibit resistance to peptidyltransferase inhibitors. The L3 mutants per se are also provided as well as cells (e.g., prokaryotic cells including bacteria and eucaryotic cells such as yeast) transformed with the nucleic acids, as well as compositions containing the mutant and a carrier.

Other aspects of the present invention pertain to reducing the toxicity of single chain RIPs in cells other than plant cells. The method entails co-administering (e.g., co-expressing) to a cell the RIP and an L3 protein. In preferred embodiments, the cell is a bacterial cell such as *E. coli* transformed with a nucleic acid encoding wild type PAP or a PAP mutant and another nucleic acid encoding the L3 protein. In more preferred embodiments, the L3 protein is a non-naturally occurring mutant as described herein.

DETAILED DESCRIPTION

Transgenic plants expressing L3 or an L3 mutant exhibit broad spectrum resistance to viruses and fungi. L3 nucleic acids useful in the present invention may be obtained from a variety of natural sources including yeast, higher plants and, animals. By the term "exogenous" it is meant in addition to the native genome of the plant. By the term "homologous" it is meant within the same species of organism (e.g., introducing a tomato gene encoding L3 into a tomato). Thus, the present invention embraces transgenic plants producing multiple copies of its own endogenous L3 gene. By "heterologous" it is meant that the L3 gene is derived or obtained from a different species of organism from the plant (e.g., an L3 nucleic acid derived from yeast or another higher plant species). Thus, "exogenous" embraces homologous and heterologous L3 nucleic acids. The nucleotide sequence (SEQ ID NO: 1) and corresponding amino acid sequence (SEQ ID NO: 2) of the yeast wild-type L3 protein (known as rpl3) are set forth below.

```
ATGTCTCACAGAAAGTACGAAGCACCACGTCACGGTCATTTAGGTTTCTTGCCAA
GAAAG
   1    ---------+---------+---------+---------+---------+---------+
                                                                    60
TACAGAGTGTCTTTCATGCTTCGTGGTGCAGTGCCAGTAAATCCAAAGAACGGTT
CTTTC
a    M  S  H  R  K  Y  E  A  P  R  H  G  H  L  G  F  L  P  R  K  -

AGAGCTGCCTCCATCAGAGCTAGAGTTAAGGCTTTTCCAAAGGATGACAGATCC
AAGCCA
  61 ---------+---------+---------+---------+---------+---------+ 120
TCTCGACGGAGGTAGTCTCGATCTCAATTCCGAAAAGGTTTCCTACTGTCTAGGT
TCGGT
a    R  A  A  S  I  R  A  R  V  K  A  F  P  K  D  D  R  S  K  P  -

GTTGCTCTAACTTCCTTCTTGGGTTACAAGGCTGGTATGACCACCATTGTCAGAG
ATTTG
 121 ---------+---------+---------+---------+---------+---------+ 180
CAACGAGATTGAAGGAAGAACCCAATGTTCCGACCATACTGGTGGTAACAGTCT
CTAAAC
a    V  A  L  T  S  F  L  G  Y  K  A  G  M  T  T  I  V  R  D  L  -

GACAGACCAGGTTCTAAGTTCCACAAGCGTGAAGTTGTCGAAGCTGTCACCGTTG
TTGAC
 181 ---------+---------+---------+---------+---------+---------+ 240
CTGTCTGGTCCAAGATTCAAGGTGTTCGCACTTCAACAGCTTCGACAGTGGCAAC
AACTG
a    D  R  P  G  S  K  F  H  K  R  E  V  V  E  A  V  T  V  V  D  -

ACTCCACCAGTTGTCGTTGTTGGTGTTGTCGGTTACGTCGAAACCCCAAGAGGTT
TGAGA
 241 ---------+---------+---------+---------+---------+---------+ 300
TGAGGTGGTCAACAGCAACAACCACAACAGCCAATGCAGCTTTGGGGTTCTCCA
AACTCT
a    T  P  P  V  V  V  G  V  V  G  Y  V  E  T  P  R  G  L  R  -

TCTTTGACCACCGTCTGGGCTGAACATTTGTCTGACGAAGTCAAGAGAAGATTCT
ACAAG
 301 ---------+---------+---------+---------+---------+---------+ 360
AGAAACTGGTGGCAGACCCGACTTGTAAACAGACTGCTTCAGTTCTCTTCTAAGA
TGTTC
a    S  L  T  T  V  W  A  E  H  L  S  D  E  V  K  R  R  F  Y  K  -

AACTGGTACAAGTCTAAGAAGAAGGCTTTCACCAAATACTCTGCCAAGTACGCTC
AAGAT
 361 ---------+---------+---------+---------+---------+---------+ 420
TTGACCATGTTCAGATTCTTCTTCCGAAAGTGGTTTATGAGACGGTTCATGCGAG
```

```
                                         -continued
TTCTA a    N  W  Y  K  S  K  K  K  A  F  T  K  Y  S  A  K  Y  A  Q  D  -

GGTGCTGGTATTGAAAGAGAATTGGCTAGAATCAAGAAGTACGCTTCCGTCGTC

AGAGTT

421 ---------+---------+---------+---------+---------+---------+ 480

CCACGACCATAACTTTCTCTTAACCGATCTTAGTTCTTCATGCGAAGGCAGCAGT

CTCAA a    G  A  G  I  E  R  E  L  A  R  I  K  K  Y  A  S  V  V  R  V  -

TTGGTCCACACTCAAATCAGAAAGACTCCATTGGCTCAAAAGAAGGCTCATTTGG

CTGAA

481 ---------+---------+---------+---------+---------+---------+ 540

AACCAGGTGTGAGTTTAGTCTTTCTGAGGTAACCGAGTTTTCTTCCGAGTAAACC

GACTT a    L  V  H  T  Q  I  R  K  T  P  L  A  Q  K  K  A  H  L  A  E  -

ATCCAATTGAACGGTGGTTCCATCTCTGAAAAGGTTGACTGGGCTCGTGAACATT

TCGAA

541 ---------+---------+---------+---------+---------+---------+ 600

TAGGTTAACTTGCCACCAAGGTAGAGACTTTTCCAACTGACCCGAGCACTTGTAA

AGCTT a    I  Q  L  N  G  G  S  I  S  E  K  V  D  W  A  R  E  H  F  E  -

AAGACTGTTGCTGTCGACAGCGTTTTTGAACAAAACGAAATGATTGACGCTATTG

CTGTC

601 ---------+---------+---------+---------+---------+---------+ 660

TTCTGACAACGACAGCTGTCGCAAAAACTTGTTTTGCTTTACTAACTGCGATAAC

GACAG a    K  T  V  A  V  D  S  V  F  E  Q  N  E  M  I  D  A  I  A  V  -

ACCAAGGGTCACGGTTTCGAAGGTGTTACCCACAGATGGGGTACTAAGAAATTG

CCAAGA

661 ---------+---------+---------+---------+---------+---------+ 720

TGGTTCCCAGTGCCAAAGCTTCCACAATGGGTGTCTACCCCATGATTCTTTAACG

GTTCT a    T  K  G  H  G  F  E  G  V  T  H  R  W  G  T  K  K  L  P  R  -

AAGACTCACAGAGGTCTAAGAAAGGTTGCTTGTATTGGTGCTTGGCATCCAGCCC

ACGTT

721 ---------+---------+---------+---------+---------+---------+ 780

TTCTGAGTGTCTCCAGATTCTTTCCAACGAACATAACCACGAACGGTAGGTCGGG

TGCAA
```

```
a   K T H R G L R K V A C I G A W H P A H V -

ATGTGGAGTGTTGCCAGAGCTGGTCAAAGAGGTTACCATTCCAGAACCTCCATTA

ACCAC

781 ---------+---------+---------+---------+---------+---------+ 840

TACACCTCACAACGGTCTCGACCAGTTTCTCCAATGGTAAGGTCTTGGAGGTAAT

TGGTG a   M W S V A R A G Q R G Y H S R T S I N H -

AAGATTTACAGAGTCGGTAAGGGTGATGATGAAGCTAACGGTGCTACCAGCTTC

GACAGA

841 ---------+---------+---------+---------+---------+---------+ 900

TTCTAAATGTCTCAGCCATTCCCACTACTACTTCGATTGCCACGATGGTCGAAGCT

GTCT a   K I Y R V G K G D D E A N G A T S F D R -

ACCAAGAAGACTATTACCCCAATGGGTGGTTTCGTCCACTACGGTGAAATTAAGA

ACGAC

901 ---------+---------+---------+---------+---------+---------+ 960

TGGTTCTTCTGATAATGGGGTTACCCACCAAAGCAGGTGATGCCACTTTAATTCT

TGCTG a   T K K T I T P M G G F V H Y G E I K N D -

TTCATCATGGTTAAAGGTTGTATCCCAGGTAACAGAAAGAGAATTGTTACTTTGA

GAAAG

961 ---------+---------+---------+---------+---------+---------+ 1020

AAGTAGTACCAATTTCCAACATAGGGTCCATTGTCTTTCTCTTAACAATGAAACT

CTTTC a   F I M V K G C I P G N R K R I V T L R K -

TCTTTGTACACCAACACTTCTAGAAAGGCTTTGGAAGAAGTCAGCTTGAAGTGGA

TTGAC

1021 ---------+---------+---------+---------+---------+---------+ 1080

AGAAACATGTGGTTGTGAAGATCTTTCCGAAACCTTCTTCAGTCGAACTTCACCT

AACTG a   S L Y T N T S R K A L E E V S L K W I D -

ACTGCTTCTAAGTTCGGTAAGGGTAGATTCCAAACCCCAGCTGAAAAGCATGCTT

TCATG

1081 ---------+---------+---------+---------+---------+---------+ 1140

TGACGAAGATTCAAGCCATTCCCATCTAAGGTTTGGGGTCGACTTTTCGTACGAA

AGTAC a   T A S K F G K G R F Q T P A E K H A F M -

GGTACTTTGAAGAAGGACTTGTAA
```

-continued
```
1141 ---------+---------+---- 1164
     CCATGAAACTTCTTCCTGAACATT a     G  T  L  K  K  D  L  *  -
```

L3 nucleic acids cloned from *Arabidopsis* and rice are described in Kim, et al., Gene 93:177–182 (1990), and Nishi, et al., Biochim. Biophys. Acta 1216:110–112 (1993) respectively. Tobacco contains two L3 genes. The nucleotide sequence (SEQ ID NO: 3) and corresponding amino acid sequence (SEQ ID NO: 4) for one tobacco L3 protein (the tobacco "8d" L3 protein) are set forth below:

```
     ATGTCTCACAGGAAGTTTGAGCATCCAAGACACGGTTCTTTGGGATTTCTGCCCA
     GGAAG
       1 ---------+---------+---------+---------+---------+---------+ 60
     TACAGAGTGTCCTTCAAACTCGTAGGTTCTGTGCCAAGAAACCCTAAAGACGGGT
     CCTTC a     M  S  H  R  K  F  E  H  P  R  H  G  S  L  G  F  L  P  R  K  -

CGTGCTGCCAGACACAGGGGAAAGGTGAAGGCATTCCCAAAAGATGATCCAAAC
     AAGCCC
      61 ---------+---------+---------+---------+---------+---------+ 120
     GCACGACGGTCTGTGTCCCCTTTCCACTTCCGTAAGGGTTTTCTACTAGGTTTGTT
     CGGG a     R  A  A  R  H  R  G  K  V  K  A  F  P  K  D  D  P  N  K  P  -

TGCAAGCTAACTGCCTTCTTGGGCTACAAAGCTGGCATGACTCACATTGTCAGAG
     ATGTT
     121 ---------+---------+---------+---------+---------+---------+ 180
     ACGTTCGATTGACGGAAGAACCCGATGTTTCGACCGTACTGAGTGTAACAGTCTC
     TACAA a     C  K  L  T  A  F  L  G  Y  K  A  G  M  T  H  I  V  R  D  V  -

GAAAAACCTGGATCAAAACTCCACAAGAAAGAGACATGTGAAGCTGTCACCATC
     ATTGAA
     181 ---------+---------+---------+---------+---------+---------+ 240
     CTTTTTGGACCTAGTTTTGAGGTGTTCTTTCTCTGTACACTTCGACAGTGGTAGTA
     ACTT a     E  K  P  G  S  K  L  H  K  K  E  T  C  E  A  V  T  I  I  E  -

ACACCTCCAATGGTGATTGTTGGTGTTGTTGGGTATGTGAAGACACCTCGTGGTC
     TTCGT
     241 ---------+---------+---------+---------+---------+---------+ 300
     TGTGGAGGTTACCACTAACAACCACAACAACCCATACACTTCTGTGGAGCACCA
     GAAGCA a     T  P  P  M  V  I  V  G  V  V  G  Y  V  K  T  P  R  G  L  R  -

TGCCTGAACACTGTCTGGGCTCAACATCTCAGTGAAGAGCTTAAGAGGAGGTTCT
     ACAAG
     301 ---------+---------+---------+---------+---------+---------+ 360
```

```
                ACGGACTTGTGACAGACCCGAGTTGTAGAGTCACTTCTCGAATTCTCCTCCAAGA
                TGTTC
         a    C  L  N  T  V  W  A  Q  H  L  S  E  E  L  K  R  R  F  Y  K  -
                AACTGGTGCAAGTCCAAGAAGAAGGCCTTCTTGAAATACTCCAAGAAATATGAA
                TCTGAT
            361 ---------+---------+---------+---------+---------+---------+ 420
                TTGACCACGTTCAGGTTCTTCTTCCGGAAGAACTTTATGAGGTTCTTTATACTTAG
                ACTA
         a    N  W  C  K  S  K  K  K  A  F  L  K  Y  S  K  K  Y  E  S  D  -
                GAAGGGAAAAAGGACATCCAGACACAGCTGGAGAAATTGAAGAAGTATGCATG
                CGTCATC
            421 ---------+---------+---------+---------+---------+---------+ 480
                CTTCCCTTTTTCCTGTAGGTCTGTGTCGACCTCTTTAACTTCTTCATACGTACGCA
                GTAG
         a    E  G  K  K  D  I  Q  T  Q  L  E  K  L  K  K  Y  A  C  V  I  -
                CGTGTTTTGGCTCACACTCAGATAAGGAAGATGAAGGGTCTGAAACAGAAGAAA
                GCCCAT
            481 ---------+---------+---------+---------+---------+---------+ 540
                GCACAAAACCGAGTGTGAGTCTATTCCTTCTACTTCCCAGACTTTGTCTTCTTTCG
                GGTA
         a    R  V  L  A  H  T  Q  I  R  K  M  K  G  L  K  Q  K  K  A  H  -
                TTGATGGAGATACAGGTGAATGGAGGGACAATTGCTCAGAAGGTTGACTTTGCA
                TATGGT
            541 ---------+---------+---------+---------+---------+---------+ 600
                AACTACCTCTATGTCCACTTACCTCCCTGTTAACGAGTCTTCCAACTGAAACGTAT
                ACCA
         a    L  M  E  I  Q  V  N  G  G  T  I  A  Q  K  V  D  F  A  Y  G  -
                TTCTTCGAGAAGCAGGTTCCAGTTGATGCTGTTTTTCAGAAGGATGAGATGATTG
                ACATC
            601 ---------+---------+---------+---------+---------+---------+ 660
                AAGAAGCTCTTCGTCCAAGGTCAACTACGACAAAAAGTCTTCCTACTCTACTAAC
                TGTAG
         a    F  F  E  K  Q  V  P  V  D  A  V  F  Q  K  D  E  M  I  D  I  -
                ATTGGTGTCACCAAGGGTAAGGGTTATGAAGGTGTTGTAACTCGTTGGGGTGTGA
                CACGT
            661 ---------+---------+---------+---------+---------+---------+ 720
                TAACCACAGTGGTTCCCATTCCCAATACTTCCACAACATTGAGCAACCCCACACT
                GTGCA
         a    I  G  V  T  K  G  K  G  Y  E  G  V  V  T  R  W  G  V  T  R  -
                CTTCCTCGCAAAACCCACAGGGGTCTGCGTAAGGTTGCTTGTATTGGAGCCTGGC
```

```
                                          -continued
ACCCT

721 ---------+---------+---------+---------+---------+---------+ 780
GAAGGAGCGTTTTGGGTGTCCCCAGACGCATTCCAACGAACATAACCTCGGACC

GTGGGA a   L P R K T H R G L R K V A C I G A W H P -
GCTAGAGTTTCCTACACAGTTGCCCGTGCTGGTCAAAATGGATACCATCACCGTA

CCGAG

781 ---------+---------+---------+---------+---------+---------+ 840
CGATCTCAAAGGATGTGTCAACGGGCACGACCAGTTTTACCTATGGTAGTGGCAT

GGCTC a   A R V S Y T V A R A G Q N G Y H H R T E -
ATGAACAAGAAGGTTTACAAACTAGGGAAGGCTGGCCAAGAGTCCCATGCTGCT

GTAACT

841 ---------+---------+---------+---------+---------+---------+ 900
TACTTGTTCTTCCAAATGTTTGATCCCTTCCGACCGGTTCTCAGGGTACGACGACA

TTGA a   M N K K V Y K L G K A G Q E S H A A V T -
GATTTTGACAGGACCGAGAAAGACATTACTCCCATGGGTGGATTTCCCCATTATG

GTGTG

901 ---------+---------+---------+---------+---------+---------+ 960
CTAAAACTGTCCTGGCTCTTTCTGTAATGAGGGTACCCACCTAAAGGGGTAATAC

CACAC a   D F D R T E K D I T P M G G F P H Y G V -
GTGAAGGATGATTACCTGTTGATCAAGGGATGCTGTGTTGGTCCTAAGAAGAGG

GTTGTA

961 ---------+---------+---------+---------+---------+---------+ 1020
CACTTCCTACTAATGGACAACTAGTTCCCTACGACACAACCAGGATTCTTCTCCC

AACAT a   V K D D Y L L I K G C C V G P K K R V V -
ACCCTTCGTCAGTCCCTGCTCAACCAGACCTCTCGTGTCGCTCTTGAGGAGATTA

AGCTG

1021 ---------+---------+---------+---------+---------+---------+ 1080
TGGGAAGCAGTCAGGGACGAGTTGGTCTGGAGAGCACAGCGAGAACTCCTCTAA

TTCGAC a   T L R Q S L L N Q T S R V A L E E I K L -
AAGTTCATCGATACATCCTCAAAGTTTGGACATGGTCGCTTCCAGACCACTCAAG

AGAAG

1081 ---------+---------+---------+---------+---------+---------+ 1140
TTCAAGTAGCTATGTAGGAGTTTCAAACCTGTACCAGCGAAGGTCTGGTGAGTTC

TCTTC
```

-continued a K F I D T S S K F G H G R F Q T T Q E K -

CAGAAATTCTATGGCCGGTTGAAGGGTTAA

1141 ---------+---------+---------+ 1170

GTCTTTAAGATACCGGCCAACTTCCCAATT a Q K F Y G R L K G * -

The nucleotide sequence (SEQ ID NO: 5) and corresponding amino acid sequence (SEQ ID NO: 6) for the second tobacco L3 protein (the tobacco "10d" L3 protein) are set forth below.

ATGTCGCATCGCAAGTTTGAGCACCCAAGACACGGTTCTTTGGGATTTCTTCCAA

GGAAA

1 ---------+---------+---------+---------+---------+---------+ 60

TACAGCGTAGCGTTCAAACTCGTGGGTTCTGTGCCAAGAAACCCTAAAGAAGGTT

CCTTT a M S H R K F E H P R H G S L G F L P R K -

AGAGCAGCACGACACAGGGGCAAAGTGAAGGCTTTTCCCAAAGATGATACAACA

AAACCT

61 ---------+---------+---------+---------+---------+---------+ 120

TCTCGTCGTGCTGTGTCCCCGTTTCACTTCCGAAAAGGGTTTCTACTATGTTGTTT

TGGA a R A A R H R G K V K A F P K D D T T K P -

TGCAGGTTGACAGCTTTCCTTGGCTACAAAGCTGGTATGACTCATATTGTCAGAG

ATGTT

121 ---------+---------+---------+---------+---------+---------+ 180

ACGTCCAACTGTCGAAAGGAACCGATGTTTCGACCATACTGAGTATAACAGTCTC

TACAA a C R L T A F L G Y K A G M T H I V R D V -

GAAAAACCAGGGTCAAAACTCCATAAGAAAGAAACATGCGAACTGGTTACCATA

ATTGAA

181 ---------+---------+---------+---------+---------+---------+ 240

CTTTTTGGTCCCAGTTTTGAGGTATTCTTTCTTTGTACGCTTGACCAATGGTATTA

ACTT a E K P G S K L H K K E T C E L V T I I E -

ACGCCTCCTATGATTGTTGTTGGGGTTGTTGGCTATGTGAAAACACCACGTGGCC

TTCGC

241 ---------+---------+---------+---------+---------+---------+ 300

TGCGGAGGATACTAACAACAACCCCAACAACCGATACACTTTTGTGGTGCACCG

GAAGCG a T P P M I V V G V V G Y V K T P R G L R -

TGCCTTAGCACGGTCTGGGCTCAACATCTTAGTGAAGAGATTAAAAGGAGATTCT

ACAAG

301 ---------+---------+---------+---------+---------+---------+ 360

```
ACGGAATCGTGCCAGACCCGAGTTGTAGAATCACTTCTCTAATTTTCCTCTAAGA
TGTTC
a   C  L  S  T  V  W  A  Q  H  L  S  E  E  I  K  R  R  F  Y  K  -
AACTGGTGCATGTCCAAAAAGAAGGCCTTTGCAAAGTACTCGAAGAAGTATGAA
ACTGAT
    361 ---------+---------+---------+---------+---------+---------+ 420
TTGACCACGTACAGGTTTTTCTTCCGGAAACGTTTCATGAGCTTCTTCATACTTTG
ACTA
a   N  W  C  M  S  K  K  K  A  F  A  K  Y  S  K  K  Y  E  T  D  -
GATGGTAAGAAGGATATTAATGCGCAATTGGAGAAGATGAAGAAGTATTGTTGT
GTCATT
    421 ---------+---------+---------+---------+---------+---------+ 480
CTACCATTCTTCCTATAATTACGCGTTAACCTCTTCTACTTCTTCATAACAACACA
GTAA
a   D  G  K  K  D  I  N  A  Q  L  E  K  M  K  K  Y  C  C  V  I  -
CGTGTTTTGGCCCATACTCAGATTAGAAAAATGAAAGGTCTCAAGCAAAAGAAG
GCACAT
    481 ---------+---------+---------+---------+---------+---------+ 540
GCACAAAACCGGGTATGAGTCTAATCTTTTTACTTTCCAGAGTTCGTTTTCTTCCG
TGTA
a   R  V  L  A  H  T  Q  I  R  K  M  K  G  L  K  Q  K  K  A  H  -
CTGATGGAGATTCAGGTTAATGGTGGGGATGTTTCCCAGAAGGTTGATTATGCTT
ATGGC
    541 ---------+---------+---------+---------+---------+---------+ 600
GACTACCTCTAAGTCCAATTACCACCCCTACAAAGGGTCTTCCAACTAATACGAA
TACCG
a   L  M  E  I  Q  V  N  G  G  D  V  S  Q  K  V  D  Y  A  Y  G  -
TTCTTTGAGAAGCAGATTCCTGTTGATGCTATTTTCCAAAAGGATGAGATGATCG
ATATT
    601 ---------+---------+---------+---------+---------+---------+ 660
AAGAAACTCTTCGTCTAAGGACAACTACGATAAAAGGTTTTCCTACTCTACTAGC
TATAA
a   F  F  E  K  Q  I  P  V  D  A  I  F  Q  K  D  E  M  I  D  I  -
ATTGGTGTGACCAAAGGTAAGGGTTATGAGGGTGTGGTGACTCGTTGGGGTGTA
ACCCGT
    661 ---------+---------+---------+---------+---------+---------+ 720
TAACCACACTGGTTTCCATTCCCAATACTCCCACACCACTGAGCAACCCCACATT
GGGCA
a   I  G  V  T  K  G  K  G  Y  E  G  V  V  T  R  W  G  V  T  R  -
CTCCCACGTAAGACCCATCGTGGTCTTAGAAAGGTGGCTTGTATTGGTGCTTGGC
```

```
                                       -continued
ATCCA
    721 ---------+---------+---------+---------+---------+---------+ 780
GAGGGTGCATTCTGGGTAGCACCAGAATCTTTCCACCGAACATAACCACGAACC
GTAGGT a     L P R K T H R G L R K V A C I G A W H P -

GCACGGGTGTCATACACTGTAGCTAGGGCTGGGCAGAATGGTTATCACCATCGC
ACTGAG
    781 ---------+---------+---------+---------+---------+---------+ 840
CGTGCCCACAGTATGTGACATCGATCCCGACCCGTCTTACCAATAGTGGTAGCGT
GACTC a     A R V S Y T V A R A G Q N G Y H H R T E -

CTGAACAAGAAAGTCTACAGGCTGGGCAAGGCTGGTCAGGAGTCTCATTCTGCA
ATAACT
    841 ---------+---------+---------+---------+---------+---------+ 900
GACTTGTTCTTTCAGATGTCCGACCCGTTCCGACCAGTCCTCAGAGTAAGACGTT
ATTGA a     L N K K V Y R L G K A G Q E S H S A I T -

GAGTTTGACAGGACTGAGAAGGATATCACGCCAATGGGTGGATTTCCTCATTATG
GTATT
    901 ---------+---------+---------+---------+---------+---------+ 960
CTCAAACTGTCCTGACTCTTCCTATAGTGCGGTTACCCACCTAAAGGAGTAATAC
CATAA a     E F D R T E K D I T P M G G F P H Y G I -

GTGAAAGAAGACTTTCTGTTGATTAAGGGCTGCTGTGTTGGACCAAAGAAGCGT
GTTGTG
    961 ---------+---------+---------+---------+---------+---------+ 1020
CACTTTCTTCTGAAAGACAACTAATTCCCGACGACACAACCTGGTTTCTTCGCAC
AACAC a     V K E D F L L I K G C C V G P K K R V V -

ACTCTGAGGCAGTCTCTGTTGAATCAGACATCTAGGGTTGCATTGGAGGAGATCA
AGCTC
   1021 ---------+---------+---------+---------+---------+---------+ 1080
TGAGACTCCGTCAGAGACAACTTAGTCTGTAGATCCCAACGTAACCTCCTCTAGT
TCGAG a     T L R Q S L L N Q T S R V A L E E I K L -

AAGTTCATTGACACATCCTCCAAGTTTGGCCATGGACGCTTCCAGACTACACAGG
AGAAG
   1081 ---------+---------+---------+---------+---------+---------+ 1140
TTCAAGTAACTGTGTAGGAGGTTCAAACCGGTACCTGCGAAGGTCTGATGTGTCC
TCTTC
```

```
a   K F I D T S S K F G H G R F Q T T Q E K -

GACAAATTCTATGGACGTCTTAAAGCTTGA

1141 ---------+---------+---------+ 1170

CTGTTTAAGATACCTGCAGAATTTCGAACT a   D K F Y G R L K A * -
```

The nucleotide sequence (SEQ ID NO: 7) and corresponding amino acid sequence (SEQ ID NO: 8) for a spontaneously occurring mutant L3 gene obtained from the yeast *Saccharomyces cerevisiae* (the L3 trichodermin resistance mutant (tcm1)) are set forth below. One nucleotide change G765C results in the amino acid change W255C (Trp255Cys). See, Schultz, et al., J. Bacteriol. 155:8–14 (1983).

```
    ATGTCTCACAGAAAGTACGAAGCACCACGTCACGGTCATTTAGGTTTCTTGCCAA

GAAAG

1 ---------+---------+---------+---------+---------+---------+ 60

TACAGAGTGTCTTTCATGCTTCGTGGTGCAGTGCCAGTAAATCCAAAGAACGGTT

CTTTC a   M S H R K Y E A P R H G H L G F L P R K -

AGAGCTGCCTCCATCAGAGCTAGAGTTAAGGCTTTTCCAAAGGATGACAGATCC

AAGCCA

61 ---------+---------+---------+---------+---------+---------+ 120

TCTCGACGGAGGTAGTCTCGATCTCAATTCCGAAAAGGTTTCCTACTGTCTAGGT

TCGGT a   R A A S I R A R V K A F P K D D R S K P -

GTTGCTCTAACTTCCTTCTTGGGTTACAAGGCTGGTATGACCACCATTGTCAGAG

ATTTG

121 ---------+---------+---------+---------+---------+---------+ 180

CAACGAGATTGAAGGAAGAACCCAATGTTCCGACCATACTGGTGGTAACAGTCT

CTAAAC a   V A L T S F L G Y K A G M T T I V R D L -

GACAGACCAGGTTCTAAGTTCCACAAGCGTGAAGTTGTCGAAGCTGTCACCGTTG

TTGAC

181 ---------+---------+---------+---------+---------+---------+ 240

CTGTCTGGTCCAAGATTCAAGGTGTTCGCACTTCAACAGCTTCGACAGTGGCAAC

AACTG a   D R P G S K F H K R E V V E A V T V V D -

ACTCCACCAGTTGTCGTTGTTGGTGTTGTCGGTTACGTCGAAACCCCAAGAGGTT

TGAGA

241 ---------+---------+---------+---------+---------+---------+ 300

TGAGGTGGTCAACAGCAACAACCACAACAGCCAATGCAGCTTTGGGGTTCTCCA

AACTCT a   T P P V V V V G V V G Y V E T P R G L R -
```

```
                                 -continued
TCTTTGACCACCGTCTGGGCTGAACATTTGTCTGACGAAGTCAAGAGAAGATTCT

ACAAG

301 ---------+---------+---------+---------+---------+---------+ 360

AGAAACTGGTGGCAGACCCGACTTGTAAACAGACTGCTTCAGTTCTCTTCTAAGA

TGTTC a    S  L  T  T  V  W  A  E  H  L  S  D  E  V  K  R  R  F  Y  K  -

AACTGGTACAAGTCTAAGAAGAAGGCTTTCACCAAATACTCTGCCAAGTACGCTC

AAGAT

361 ---------+---------+---------+---------+---------+---------+ 420

TTGACCATGTTCAGATTCTTCTTCCGAAAGTGGTTTATGAGACGGTTCATGCGAG

TTCTA a    N  W  Y  K  S  K  K  K  A  F  T  K  Y  S  A  K  Y  A  Q  D  -

GGTGCTGGTATTGAAAGAGAATTGGCTAGAATCAAGAAGTACGCTTCCGTCGTC

AGAGTT

421 ---------+---------+---------+---------+---------+---------+ 480

CCACGACCATAACTTTCTCTTAACCGATCTTAGTTCTTCATGCGAAGGCAGCAGT

CTCAA a    G  A  G  I  E  R  E  L  A  R  I  K  K  Y  A  S  V  V  R  V  -

TTGGTCCACACTCAAATCAGAAAGACTCCATTGGCTCAAAAGAAGGCTCATTTGG

CTGAA

481 ---------+---------+---------+---------+---------+---------+ 540

AACCAGGTGTGAGTTTAGTCTTTCTGAGGTAACCGAGTTTTCTTCCGAGTAAACC

GACTT a    L  V  H  T  Q  I  R  K  T  P  L  A  Q  K  K  A  H  L  A  E  -

ATCCAATTGAACGGTGGTTCCATCTCTGAAAAGGTTGACTGGGCTCGTGAACATT

TCGAA

541 ---------+---------+---------+---------+---------+---------+ 600

TAGGTTAACTTGCCACCAAGGTAGAGACTTTTCCAACTGACCCGAGCACTTGTAA

AGCTT a    I  Q  L  N  G  G  S  I  S  E  K  V  D  W  A  R  E  H  F  E  -

AAGACTGTTGCTGTCGACAGCGTTTTTGAACAAAACGAAATGATTGACGCTATTG

CTGTC

601 ---------+---------+---------+---------+---------+---------+ 660

TTCTGACAACGACAGCTGTCGCAAAAACTTGTTTTGCTTTACTAACTGCGATAAC

GACAG a    K  T  V  A  V  D  S  V  F  E  Q  N  E  M  I  D  A  I  A  V  -

ACCAAGGGTCACGGTTTCGAAGGTGTTACCCACAGATGGGGTACTAAGAAATTG

CCAAGA

661 ---------+---------+---------+---------+---------+---------+ 720

TGGTTCCCAGTGCCAAAGCTTCCACAATGGGTGTCTACCCCATGATTCTTTAACG
```

-continued

```
GTTCT
a    T  K  G  H  G  F  E  G  V  T  H  R  W  G  T  K  K  L  P  R -

AAGACTCACAGAGGTCTAAGAAAGGTTGCTTGTATTGGTGCTTGCCATCCAGCCC
ACGTT
    721 ---------+---------+---------+---------+---------+---------+ 780
TTCTGAGTGTCTCCAGATTCTTTCCAACGAACATAACCACGAACGGTAGGTCGGG
TGCAA
a    K  T  H  R  G  L  R  K  V  A  C  I  G  A  C  H  P  A  H  V -

ATGTGGAGTGTTGCCAGAGCTGGTCAAAGAGGTTACCATTCCAGAACCTCCATTA
ACCAC
    781 ---------+---------+---------+---------+---------+---------+ 840
TACACCTCACAACGGTCTCGACCAGTTTCTCCAATGGTAAGGTCTTGGAGGTAAT
TGGTG
a    M  W  S  V  A  R  A  G  Q  R  G  Y  H  S  R  T  S  I  N  H -

AAGATTTACAGAGTCGGTAAGGGTGATGATGAAGCTAACGGTGCTACCAGCTTC
GACAGA
    841 ---------+---------+---------+---------+---------+---------+ 900
TTCTAAATGTCTCAGCCATTCCCACTACTACTTCGATTGCCACGATGGTCGAAGCT
GTCT
a    K  I  Y  R  V  G  K  G  D  D  E  A  N  G  A  T  S  F  D  R -

ACCAAGAAGACTATTACCCCAATGGGTGGTTTCGTCCACTACGGTGAAATTAAGA
ACGAC
    901 ---------+---------+---------+---------+---------+---------+ 960
TGGTTCTTCTGATAATGGGGTTACCCACCAAAGCAGGTGATGCCACTTTAATTCT
TGCTG
a    T  K  K  T  I  T  P  M  G  G  F  V  H  Y  G  E  I  K  N  D -

TTCATCATGGTTAAAGGTTGTATCCCAGGTAACAGAAAGAGAATTGTTACTTTGA
GAAAG
    961 ---------+---------+---------+---------+---------+---------+ 1020
AAGTAGTACCAATTTCCAACATAGGGTCCATTGTCTTTCTCTTAACAATGAAACT
CTTTC
a    F  I  M  V  K  G  C  I  P  G  N  R  K  R  I  V  T  L  R  K -

TCTTTGTACACCAACACTTCTAGAAAGGCTTTGGAAGAAGTCAGCTTGAAGTGGA
TTGAC
    1021 ---------+---------+---------+---------+---------+---------+ 1080
AGAAACATGTGGTTGTGAAGATCTTTCCGAAACCTTCTTCAGTCGAACTTCACCT
AACTG
a    S  L  Y  T  N  T  S  R  K  A  L  E  E  V  S  L  K  W  I  D -

ACTGCTTCTAAGTTCGGTAAGGGTAGATTCCAAACCCCAGCTGAAAAGCATGCTT
TCATG
```

```
                                  -continued
     1081 ---------+---------+---------+---------+---------+---------+ 1140

TGACGAAGATTCAAGCCATTCCCATCTAAGGTTTGGGGTCGACTTTTCGTACGAA

AGTAC a  T  A  S  K  F  G  K  G  R  F  Q  T  P  A  E  K  H  A  F  M  -

GGTACTTTGAAGAAGGACTTGTAA

1141 ---------+---------+---- 1164

CCATGAAACTTCTTCCTGAACATT a    G  T  L  K  K  D  L  *  -
```

Several naturally occurring fungal toxins, including trichodermin, exert a cytotoxic effect by targeting the peptidyltransferase step of elongation during protein synthesis. The fungal toxin trichodermin, for example, inhibits peptide bond formation by binding to the peptidyltransferase center (Barbacid, et al., Eur. J. Biochem. 44:437–444 (1974). In the case of anti-fungal resistance, therefore, other spontaneously occuring L3 mutants may be identified simply by determining whether cells survive in the presence of a given fungal toxin. See Fried, et al., Proc. Natl. Acad. Sci. USA 78:238–242 (1981).

Non-naturally occurring L3 mutants useful in the present invention can be identified and selected in several ways based upon one or more of several properties that they exhibit. One protocol entails randomly mutagenizing the L3 gene, introducing nucleic acid encoding the single chain RIP such as Pokeweed Antiviral Protein (PAP) into the microorganism strains harboring L3 gene, and determining if the mutant L3 confers resistance to the cytostatic effects of PAP. In preferred embodiments, isogenic null mutant strains wherein the endogenous L3 gene has been knocked out are transformed with a LEU2-based vector, e.g., pNT 188, containing a PAP cDNA under the control of a GAL1 promoter and plasmids containing the mutated L3 DNAs. Galactose induction of PAP expression does not have a cytostatic effect on the growth of the strain harboring the L3 mutant that confers resistance to PAP. In contrast, growth of cells harboring PAP DNA and wild-type L3 DNA is significantly inhibited when PAP expression is induced by galactose. Stated differently, cells harboring the L3 mutants will grow under PAP induction, whereas cells containing pRPL3 encoding wild-type L3 will not grow.

Another method of selecting L3 mutants is based on the phenomenon that maintenance of killer ("Mak") alleles are unable to maintain the M1 satellite virus. Wickner, et al., PNAS USA 79:4706–4708 (1982). M1 is an endogenous virus that is found in most naturally occurring yeast strains. It encodes a secreted toxin and an immunity factor. Yeast cells harboring M1 are able to kill cells that do not contain the virus. Such infected cells are called "killer" yeast. The ability of infected cells to kill uninfected cells is easily ascertained through a simple assay. Similarly, loss of such "killer" activity can also be monitored. These results indicate that ribosomal protein L3 is involved in the replication and maintenance of the M1 double stranded RNA of the yeast killer virus. Thus, using a killer virus assay (e.g., Tumer, et al., J. Virol. 72:1036–1042 (1998)) allows for the determination whether the L3 mutants can maintain the killer virus. The L3 mutants of the present inventin are identified by their inability to maintain the yeast killer virus (L-A-M1).

Yet another method is based upon the observation that strains harboring the Mak8-1 allele of RPL3 exhibit increased programmed frameshifting efficiencies, supporting the notion that events at the peptidyltransferase center play a critical role in programmed −1 ribosomal frameshifting. Thus, the desired L3 mutants exhibit altered programmed −1 ribosomal frameshifting efficiencies both in cells and in in vitro translation extracts as determined by the assays described in Tumer, et al., (1998) supra. In many cases, the mutants exhibit increased efficiencies but in some cases, decreased efficiencies are observed.

L3 mutants may also exhibit resistance to peptidyltransferase inhibitors. Such inhibitors include sparsomycin, anicomycin, puromycin, tricodermin, pristinamycin, gougerotinomycin, lincomycin and clindacmycin. Methods for determining whether an L3 mutant is resistant are described in Example 2.

The nucleotide (SEQ ID NO: 9) and corresponding amino acid sequences (SEQ ID NO: 10) for one Mak mutant of L3 are set forth below. Two nucleotide changes, G765C and C769T, result in two amino acid changes, namely W255C (Trp255Cys) and P257S (Pro257Ser) respectively. This mutant L3 is designated Mak8 (W255C, P257S).

```
        ATGTCTCACAGAAAGTACGAAGCACCACGTCACGGTCATTTAGGTTTCTTGCCAA

GAAAG

1 ---------+---------+---------+---------+---------+---------+ 60

TACAGAGTGTCTTTCATGCTTCGTGGTGCAGTGCCAGTAAATCCAAAGAACGGTT

CTTTC a   M  S  H  R  K  Y  E  A  P  R  H  G  H  L  G  F  L  P  R  K  -

AGAGCTGCCTCCATCAGAGCTAGAGTTAAGGCTTTTCCAAAGGATGACAGATCC
```

```
AAGCCA
    61 ---------+---------+---------+---------+---------+---------+ 120
TCTCGACGGAGGTAGTCTCGATCTCAATTCCGAAAAGGTTTCCTACTGTCTAGGT

TCGGT
a   R A A S I R A R V K A F P K D D R S K P -
GTTGCTCTAACTTCCTTCTTGGGTTACAAGGCTGGTATGACCACCATTGTCAGAG

ATTTG
   121 ---------+---------+---------+---------+---------+---------+ 180
CAACGAGATTGAAGGAAGAACCCAATGTTCCGACCATACTGGTGGTAACAGTCT

CTAAAC
a   V A L T S F L G Y K A G M T T I V R D L -
GACAGACCAGGTTCTAAGTTCCACAAGCGTGAAGTTGTCGAAGCTGTCACCGTTG

TTGAC
   181 ---------+---------+---------+---------+---------+---------+ 240
CTGTCTGGTCCAAGATTCAAGGTGTTCGCACTTCAACAGCTTCGACAGTGGCAAC

AACTG
a   D R P G S K F H K R E V V E A V T V V D -
ACTCCACCAGTTGTCGTTGTTGGTGTTGTCGGTTACGTCGAAACCCCAAGAGGTT

TGAGA
   241 ---------+---------+---------+---------+---------+---------+ 300
TGAGGTGGTCAACAGCAACAACCACAACAGCCAATGCAGCTTTGGGGTTCTCCA

AACTCT
a   T P P V V V V G V V G Y V E T P R G L R -
TCTTTGACCACCGTCTGGGCTGAACATTTGTCTGACGAAGTCAAGAGAAGATTCT

ACAAG
   301 ---------+---------+---------+---------+---------+---------+ 360
AGAAACTGGTGGCAGACCCGACTTGTAAACAGACTGCTTCAGTTCTCTTCTAAGA

TGTTC
a   S L T T V W A E H L S D E V K R R F Y K -
AACTGGTACAAGTCTAAGAAGAAGGCTTTCACCAAATACTCTGCCAAGTACGCTC

AAGAT
   361 ---------+---------+---------+---------+---------+---------+ 420
TTGACCATGTTCAGATTCTTCTTCCGAAAGTGGTTTATGAGACGGTTCATGCGAG

TTCTA
a   N W Y K S K K K A F T K Y S A K Y A Q D -
GGTGCTGGTATTGAAAGAGAATTGGCTAGAATCAAGAAGTACGCTTCCGTCGTC

AGAGTT
   421 ---------+---------+---------+---------+---------+---------+ 480
CCACGACCATAACTTTCTCTTAACCGATCTTAGTTCTTCATGCGAAGGCAGCAGT

CTCAA
```

```
a  G A G I E R E L A R I K K Y A S V V R V -

TTGGTCCACACTCAAATCAGAAAGACTCCATTGGCTCAAAAGAAGGCTCATTTGG
    CTGAA
    481 ---------+---------+---------+---------+---------+---------+ 540
    AACCAGGTGTGAGTTTAGTCTTTCTGAGGTAACCGAGTTTTCTTCCGAGTAAACC
    GACTT a  L V H T Q I R K T P L A Q K K A H L A E -

ATCCAATTGAACGGTGGTTCCATCTCTGAAAAGGTTGACTGGGCTCGTGAACATT
    TCGAA
    541 ---------+---------+---------+---------+---------+---------+ 600
    TAGGTTAACTTGCCACCAAGGTAGAGACTTTTCCAACTGACCCGAGCACTTGTAA
    AGCTT a  I Q L N G G S I S E K V D W A R E H F E -

AAGACTGTTGCTGTCGACAGCGTTTTTGAACAAAACGAAATGATTGACGCTATTG
    CTGTC
    601 ---------+---------+---------+---------+---------+---------+ 660
    TTCTGACAACGACAGCTGTCGCAAAAACTTGTTTTGCTTTACTAACTGCGATAAC
    GACAG a  K T V A V D S V F E Q N E M I D A I A V -

ACCAAGGGTCACGGTTTCGAAGGTGTTACCCACAGATGGGGTACTAAGAAATTG
    CCAAGA
    661 ---------+---------+---------+---------+---------+---------+ 720
    TGGTTCCCAGTGCCAAAGCTTCCACAATGGGTGTCTACCCCATGATTCTTTAACG
    GTTCT a  T K G H G F E G V T H R W G T K K L P R -

AAGACTCACAGAGGTCTAAGAAAGGTTGCTTGTATTGGTGCTTGCCATTCAGCCC
    ACGTT
    721 ---------+---------+---------+---------+---------+---------+ 780
    TTCTGAGTGTCTCCAGATTCTTTCCAACGAACATAACCACGAACGGTAGGTCGGG
    TGCAA a  K T H R G L R K V A C I G A C H S A H V -

ATGTGGAGTGTTGCCAGAGCTGGTCAAAGAGGTTACCATTCCAGAACCTCCATTA
    ACCAC
    781 ---------+---------+---------+---------+---------+---------+ 840
    TACACCTCACAACGGTCTCGACCAGTTTCTCCAATGGTAAGGTCTTGGAGGTAAT
    TGGTG a  M W S V A R A G Q R G Y H S R T S I N H -

AAGATTTACAGAGTCGGTAAGGGTGATGATGAAGCTAACGGTGCTACCAGCTTC
    GACAGA
    841 ---------+---------+---------+---------+---------+---------+ 900
```

```
TTCTAAATGTCTCAGCCATTCCCACTACTACTTCGATTGCCACGATGGTCGAAGCT
GTCT
a   K I Y R V G K G D D E A N G A T S F D R -
ACCAAGAAGACTATTACCCCAATGGGTGGTTTCGTCCACTACGGTGAAATTAAGA
ACGAC
    901 ---------+---------+---------+---------+---------+---------+ 960
TGGTTCTTCTGATAATGGGGTTACCCACCAAAGCAGGTGATGCCACTTTAATTCT
TGCTG
a   T K K T I T P M G G F V H Y G E I K N D -
TTCATCATGGTTAAAGGTTGTATCCCAGGTAACAGAAAGAGAATTGTTACTTTGA
GAAAG
    961 ---------+---------+---------+---------+---------+---------+ 1020
AAGTAGTACCAATTTCCAACATAGGGTCCATTGTCTTTCTCTTAACAATGAAACT
CTTTC
a   F I M V K G C I P G N R K R I V T L R K -
TCTTTGTACACCAACACTTCTAGAAAGGCTTTGGAAGAAGTCAGCTTGAAGTGGA
TTGAC
   1021 ---------+---------+---------+---------+---------+---------+ 1080
AGAAACATGTGGTTGTGAAGATCTTTCCGAAACCTTCTTCAGTCGAACTTCACCT
AACTG
a   S L Y T N T S R K A L E E V S L K W I D -
ACTGCTTCTAAGTTCGGTAAGGGTAGATTCCAAACCCCAGCTGAAAAGCATGCTT
TCATG
   1081 ---------+---------+---------+---------+---------+---------+ 1140
TGACGAAGATTCAAGCCATTCCCATCTAAGGTTTGGGGTCGACTTTTCGTACGAA
AGTAC
a   T A S K F G K G R F Q T P A E K H A F M -
    GGTACTTTGAAGAAGGACTTGTAA
   1141 ---------+---------+---- 1164
    CCATGAAACTTCTTCCTGAACATT
a   G T L K K D L * -
```

The nucleotide (SEQ ID NO: 11) and corresponding amino acid sequences (SEQ ID NO: 12) for another L3 mutant ("rpl-T845C") are set forth below.

One nucleotide change, T845C, results in the amino acid change I282T (Iso282Thr).

```
ATGTCTCACAGAAAGTACGAAGCACCACGTCACGGTCATTTAGGTTTCTTGCCAA
GAAAG
      1 ---------+---------+---------+---------+---------+---------+ 60
TACAGAGTGTCTTTCATGCTTCGTGGTGCAGTGCCAGTAAATCCAAAGAACGGTT
CTTTC
a   M S H R K Y E A P R H G H L G F L P R K -
```

-continued

```
AGAGCTGCCTCCATCAGAGCTAGAGTTAAGGCTTTTCCAAAGGATGACAGATCC
AAGCCA
    61 ---------+---------+---------+---------+---------+---------+ 120
TCTCGACGGAGGTAGTCTCGATCTCAATTCCGAAAAGGTTTCCTACTGTCTAGGT
TCGGT
  a   R  A  A  S  I  R  A  R  V  K  A  F  P  K  D  D  R  S  K  P -
GTTGCTCTAACTTCCTTCTTGGGTTACAAGGCTGGTATGACCACCATTGTCAGAG
ATTTG
   121 ---------+---------+---------+---------+---------+---------+ 180
CAACGAGATTGAAGGAAGAACCCAATGTTCCGACCATACTGGTGGTAACAGTCT
CTAAAC
  a   V  A  L  T  S  F  L  G  Y  K  A  G  M  T  T  I  V  R  D  L -
GACAGACCAGGTTCTAAGTTCCACAAGCGTGAAGTTGTCGAAGCTGTCACCGTTG
TTGAC
   181 ---------+---------+---------+---------+---------+---------+ 240
CTGTCTGGTCCAAGATTCAAGGTGTTCGCACTTCAACAGCTTCGACAGTGGCAAC
AACTG
  a   D  R  P  G  S  K  F  H  K  R  E  V  V  E  A  V  T  V  V  D -
ACTCCACCAGTTGTCGTTGTTGGTGTTGTCGGTTACGTCGAAACCCCAAGAGGTT
TGAGA
   241 ---------+---------+---------+---------+---------+---------+ 300
TGAGGTGGTCAACAGCAACAACCACAACAGCCAATGCAGCTTTGGGGTTCTCCA
AACTCT
  a   T  P  P  V  V  V  V  G  V  V  G  Y  V  E  T  P  R  G  L  R -
TCTTTGACCACCGTCTGGGCTGAACATTTGTCTGACGAAGTCAAGAGAAGATTCT
ACAAG
   301 ---------+---------+---------+---------+---------+---------+ 360
AGAAACTGGTGGCAGACCCGACTTGTAAACAGACTGCTTCAGTTCTCTTCTAAGA
TGTTC
  a   S  L  T  T  V  W  A  E  H  L  S  D  E  V  K  R  R  F  Y  K -
AACTGGTACAAGTCTAAGAAGAAGGCTTTCACCAAATACTCTGCCAAGTACGCTC
AAGAT
   361 ---------+---------+---------+---------+---------+---------+ 420
TTGACCATGTTCAGATTCTTCTTCCGAAAGTGGTTTATGAGACGGTTCATGCGAG
TTCTA
  a   N  W  Y  K  S  K  K  K  A  F  T  K  Y  S  A  K  Y  A  Q  D -
GGTGCTGGTATTGAAAGAGAATTGGCTAGAATCAAGAAGTACGCTTCCGTCGTC
AGAGTT
   421 ---------+---------+---------+---------+---------+---------+ 480
CCACGACCATAACTTTCTCTTAACCGATCTTAGTTCTTCATGCGAAGGCAGCAGT
```

```
CTCAA
a   G A G I E R E L A R I K K Y A S V V R V -
TTGGTCCACACTCAAATCAGAAAGACTCCATTGGCTCAAAAGAAGGCTCATTTGG
CTGAA
    481 ---------+---------+---------+---------+---------+---------+ 540
AACCAGGTGTGAGTTTAGTCTTTCTGAGGTAACCGAGTTTTCTTCCGAGTAAACC
GACTT
a   L V H T Q I R K T P L A Q K K A H L A E -
ATCCAATTGAACGGTGGTTCCATCTCTGAAAAGGTTGACTGGGCTCGTGAACATT
TCGAA
    541 ---------+---------+---------+---------+---------+---------+ 600
TAGGTTAACTTGCCACCAAGGTAGAGACTTTTCCAACTGACCCGAGCACTTGTAA
AGCTT
a   I Q L N G G S I S E K V D W A R E H F E -
AAGACTGTTGCTGTCGACAGCGTTTTTGAACAAAACGAAATGATTGACGCTATTG
CTGTC
    601 ---------+---------+---------+---------+---------+---------+ 660
TTCTGACAACGACAGCTGTCGCAAAAACTTGTTTTGCTTTACTAACTGCGATAAC
GACAG
a   K T V A V D S V F E Q N E M I D A I A V -
ACCAAGGGTCACGGTTTCGAAGGTGTTACCCACAGATGGGGTACTAAGAAATTG
CCAAGA
    661 ---------+---------+---------+---------+---------+---------+ 720
TGGTTCCCAGTGCCAAAGCTTCCACAATGGGTGTCTACCCCATGATTCTTTAACG
GTTCT
a   T K G H G F E G V T H R W G T K K L P R -
AAGACTCACAGAGGTCTAAGAAAGGTTGCTTGTATTGGTGCTTGGCATCCAGCCC
ACGTT
    721 ---------+---------+---------+---------+---------+---------+ 780
TTCTGAGTGTCTCCAGATTCTTTCCAACGAACATAACCACGAACGGTAGGTCGGG
TGCAA
a   K T H R G L R K V A C I G A W H P A H V -
ATGTGGAGTGTTGCCAGAGCTGGTCAAAGAGGTTACCATTCCAGAACCTCCATTA
ACCAC
    781 ---------+---------+---------+---------+---------+---------+ 840
TACACCTCACAACGGTCTCGACCAGTTTCTCCAATGGTAAGGTCTTGGAGGTAAT
TGGTG
a   M W S V A R A G Q R G Y H S R T S I N H -
AAGACTTACAGAGTCGGTAAGGGTGATGATGAAGCTAACGGTGCTACCAGCTTC
GACAGA
```

-continued

```
   841 ---------+---------+---------+---------+---------+---------+ 900
TTCTGAATGTCTCAGCCATTCCCACTACTACTTCGATTGCCACGATGGTCGAAGCT
GTCT
a    K T Y R V G K G D D E A N G A T S F D R -

ACCAAGAAGACTATTACCCCAATGGGTGGTTTCGTCCACTACGGTGAAATTAAGA
ACGAC
   901 ---------+---------+---------+---------+---------+---------+ 960
TGGTTCTTCTGATAATGGGGTTACCCACCAAAGCAGGTGATGCCACTTTAATTCT
TGCTG
a    T K K T I T P M G G F V H Y G E I K N D -

TTCATCATGGTTAAAGGTTGTATCCCAGGTAACAGAAAGAGAATTGTTACTTTGA
GAAAG
   961 ---------+---------+---------+---------+---------+---------+ 1020
AAGTAGTACCAATTTCCAACATAGGGTCCATTGTCTTTCTCTTAACAATGAAACT
CTTTC
a    F I M V K G C I P G N R K R I V T L R K -

TCTTTGTACACCAACACTTCTAGAAAGGCTTTGGAAGAAGTCAGCTTGAAGTGGA
TTGAC
  1021 ---------+---------+---------+---------+---------+---------+ 1080
AGAAACATGTGGTTGTGAAGATCTTTCCGAAACCTTCTTCAGTCGAACTTCACCT
AACTG
a    S L Y T N T S R K A L E E V S L K W I D -

ACTGCTTCTAAGTTCGGTAAGGGTAGATTCCAAACCCCAGCTGAAAAGCATGCTT
TCATG
  1081 ---------+---------+---------+---------+---------+---------+ 1140
TGACGAAGATTCAAGCCATTCCCATCTAAGGTTTGGGGTCGACTTTTCGTACGAA
AGTAC
a    T A S K F G K G R F Q T P A E K H A F M -

GGTACTTTGAAGAAGGACTTGTAA
  1141 ---------+---------+---- 1164
     CCATGAAACTTCTTCCTGAACATT
a    G T L K K D L * -
```

The L3 nucleic acids of the present invention can be prepared in accordance with standard procedures. Likewise, preparation of expression cassettes and vectors for the introduction of the L3 nucleic acid into plant cells, protoplasts, whole plants and plant parts are also well known in the art. In the case of monocot transformation, for example, preferred promoters include the CaMV 35S promoter, ubiquitin promoter, and the actin promoter. The L3 proteins per se may be produced in accordance with standard techniques, preferably via genetic engineering.

In other preferred embodiments, nucleic acids encoding L3 and L3 mutants are introduced into plants in concert with wild-type PAP, variant PAP (i.e. PAP-v, which differs from wild-type PAP in terms of the double amino acid substitutions, Leu20Arg and Tyr49His), PAP mutants having reduced phytotoxicity compared to wild-type PAP or PAP-v, and which have intact catalytic active site amino acid residues (Glu176G and Arg179), and PAP II. Wild-type PAP, PAP-v and various PAP mutants are described in U.S. Pat. No. 5,756,322. PAP II is reported in Poyet, et al., FEBS Letters 347:268–272 (1994). The term “PAP-II,” is inclusive of the 310 amino acid polypeptide disclosed in Poyet et al., the 285-amino acid polypeptide containing amino acid residues 26–310 of said polypeptide (i.e., “PAP II (1-285)”) and which excludes the N-terminal twenty-five-amino acid signal sequence and analogs of PAP II (1-285) such as fragments and mutants (e.g., amino acid additions, deletions and substitutions) that substantially retain PAP II anti-viral and anti-fungal properties and exhibit reduced phytotoxicity compared to PAP. PAP II mutants are described in WO 99/60843, published Dec. 2, 1999. Constructs, other intermediates and methods for preparing transgenic plants expressing these PAPs (as well as plant cells and protoplasts transfected with the PAP nucleic acids) are also described therein. These teachings are also applicable to L3. It is preferred to place the L3 and PAP nucleic acids under the control of separate regulatory units and polyadenylation sites.

L3 can be introduced and expressed in a variety of higher plants including monocots (e.g., cereal crops) and dicots in accordance with standard transformation techniques for the plant type of interest. See U.S. Pat. No. 5,675,322 (and references cited therein), Horsch, et al., Science 227:1229–1231 (1985); and Hartman, et al., Bio/technology 12:919–923 (1994). Specific examples include maize, tomato, turfgrass, asparagus, papaya, sunflower, rye, beans, ginger, lotus, bamboo, potato, rice, peanut, barley, malt, wheat, alfalfa, soybean, oat, eggplant, squash, onion, broccoli, sugarcane, sugar beet, beets, apples, oranges, grapefruit, pear, plum, peach, pineapple, grape, rose, carnation, daisy, tulip, Douglas fir, cedar, white pine, scotch pine, spruce, peas, cotton, flax, canola, ornamentals and coffee.

Transgenic plants expressing L3 nucleic acid exhibit increased resistance to plant viruses, including but not limited to RNA viruses e.g., citrus tristeza virus, potexviruses such as (PVX, potato virus X), potyvirus (PVY), cucumber mosaic virus (CMV), tobacco mosaic viruses (TMV), barley yellow dwarf virus (BYDV), wheat streak mosaic virus, potato leaf roll virus (PLRV), plumpox virus, watermelon mosaic virus, zucchini yellow mosaic virus, papaya ringspot virus, beet western yellow virus, soybean dwarf virus, carrot read leaf virus and DNA plant viruses such as tomato yellow leaf curl virus. See also Lodge, et al., PNAS USA 90:7089–7093 (1993); Tomlinson, et al., J. Gen. Virol. 22:225–232 (1974); and Chen, et al., Plant Pathol. 40:612–620 (1991).

Expression of L3 genes also provides increased resistance to diseases caused by plant fungi, including those caused by *Fusarium* (causing root rot of bean, dry rot of potatoes, head blight (scab) in wheat), *Pythium* (one of the causes of seed rot, seedling damping off and root rot), *Phytophthora* (the cause of late blight of potato and of root rots, and blights of many other plants), *Bremia, Peronospora, Plasmopara, Pseudoperonospora* and *Sclerospora* (causing downy mildews), *Erysiphe graminis* (causing powdery mildew of cereals and grasses), *Verticillium* (causing vascular wilts of vegetables, flowers, crop plants and trees), *Rhizoctonia* (causing damping off disease of many plants and brown patch disease of turfgrasses), *Cochliobolus* (causing root and foot rot, and also blight of cereals and grasses), *Giberella* (causing seedling blight and foot or stalk rot of corn and small grains), *Gaeumannomyces* (causing the take-all and whiteheads disease of cereals), *Schlerotinia* (causing crown rots and blights of flowers and vegetables and dollar spot disease of turfgrasses), *Puccinia* (causing the stem rust of wheat and other small grains), *Ustilago* (causing corn smut), *Magnaporthae* (causing summer patch of turfgrasses), and *Schlerotium* (causing southern blight of turfgrasses). Other important fungal diseases include those caused by *Cercospora, Septoria, Mycosphoerella, Glomerella, Colletotrichum, Helminthosporium, Alterneria, Botrytis, Cladosporium* and *Aspergillus*.

Trichothecenes are a class of toxic, sesquiterpenoid secondary metabolites that are produced mainly by plant pathogenic fungi (Fernandez-Lobato et al., Biochem. J. 267: 709–713 (1990). Trichodermin is a member of this group of toxins. *Fusarium graminearum* and *F. culmorum* produce the trichothecene mycotoxin deoxynivalenol, which contaminates a substantial portion of agricultural crops such as wheat, barley and maize. Trichothecene resistance may be attained through a mutation in L3 e.g., tcm1, resulting in decreased fungal infection.

The L3 proteins of the present invention may also be introduced into other eukaryotic cells e.g., animal cells to reduce the cytotoxic effect of various pharmaceutical and therapeutic agents that contain single-chain RIPs. The cytotoxic effect of these RIPs is mediated by binding to endogenous L3 proteins in the cell. A preferred embodiment entails co-administration of a composition containing an L3 protein along with the RIP. The RIP may be administered in conjugated form to a ligand that recognizes a receptor on a target cell surface. By co-administration, it is meant administration of the L3 protein suitably prior to, simultaneously with or after the administration of the RIP such that the L3 will be present in the cell to reduce to cytotoxic effect of the RIP on various cells, particularly non-diseased cells. In more preferred embodiments, the L3 protein is a non-naturally occurring mutant as described herein.

Yet another use of the L3 proteins concerns the production of single chain RIPs such as PAP in prokaryotic cells such as *E. coli*. PAP, for example, is toxic to *E. coli*, particularly when expressed in high amounts. Co-administration or co-expression of an L3 protein in the prokaryote (e.g., bacterium) reduces the toxicity of the RIP and allows greater production of the recombinant RIP. By "co-expression" it is meant introducing an exogenous nucleic acid encoding an L3 protein of the present invention into the prokaryotic cell along with the nucleic acid encoding the RIP. Regardless of the manner in which the cell is treated so as to contain the L3 protein, what is important is that the L3 protein is present in the cell when PAP is produced so as to reduce the cytotoxicity of the RIP. While not intending to be bound by theory, Applicants believe that because L3 is highly conserved between prokaryotes and eukaryotes, the RIP binds endogenous L3 protein in the prokaryote.

The invention will be further described by reference to the following detailed examples. These examples are provided for purposes of illustration only and are not intended to be limiting as to the scope of the invention described herein, unless otherwise specified.

EXAMPLE 1

Pokeweed Antiviral Protein Accesses Ribosomes by Binding to L3

Pokeweed antiviral protein (PAP), a 29 kDa ribosome-inactivating protein (RIP), catalytically removes an adenine residue from the conserved a-sarcinloop of the large rRNA, thereby preventing the binding of eEF-2/GTP complex during protein elongation. Since the a-sarcin loop has been placed near the peptidyl transferase center in *E. coli* ribosomes, we investigated the effects of alterations at the peptidyl transferase center on the activity of PAP. We demonstrate here that a chromosomal mutant of yeast, harboring the mak8-1 allele of peptidyl transferase-linked ribosomal protein L3 (RPL3), is resistant to the cytostatic effects of PAP. Unlike wild-type yeast, ribosomes from mak8-1 cells are not depurinated when PAP expression is induced in vivo, indicating that wild-type L3 is required for ribosome depurination. Co-immunoprecipitation studies show that PAP binds directly to L3 or Mak8-1p in vitro, but does not physically interact with ribosome associated Mak8-1p. L3 is required for PAP to bind to ribosomes and depurinate the 25S rRNA, suggesting that it is located in close proximity to the a-sarcin loop. These results demonstrate for the first time that a ribosomal protein provides a receptor site for an RIP and allows depurination of the target adenine.

The abbreviations used are as follows: PAP, pokeweed antiviral protein; RIP, ribosomal inactivating protein; eEF-2, eukaryotic elongation factor 2.

Experimental Procedures

Yeast strains and vectors. The cDNAs encoding PAP (NT188) and PAPx (NT224) were introduced as SmaI/BglII fragments into the yeast expression vectorYEp351. PAPx is an active site mutant of PAP with a point mutation (E176V), which abolishes enzymatic activity. Hur, et al., Proc. Natl. Acad. Sci. US 92:8448–8452 (1995). Transcription of the cDNAs was under the control of a galactose-inducible GAL1 promoter. Vectors containing PAP or PAPx were transformed (Ito, et al., J. Bacteriol. 153:163–168 (1983)) into the yeast strains *S. cerevisiae* W303 (MATα, ade2-1 trpl1-1 ura3-1 leu2-3, 112 his3-11, 15can1-100), 1906 (MATα, leu2 mak8-1), or the isogenic strains JD980 (MATα lys2 his3 ura3 leu2Δ trp1Δ RPL3Δ::hisG), containing either pRPL3 or pmak8-1 (as described in Example 2, now Peltz, et al., Mol. Cell. Biol. 19(1):384–391 (1999)). YEp351 transformed into all cell types was used as a negative control.

Yeast growth and time course induction. Yeast cells were grown in 300 ml of H-Leu medium (See, Treco, et al., *Current Protocols in Molecular Biology*, Ausubel, et al., eds. Wiley (1993)); with 2% raffinose at 30° C. to an $A_{600}$=0.6. Aliquot for protein analysis (2 ml), RNA extraction (15 ml) and ribosome isolation (25 ml) were removed and pelleted by centrifugation at 2,000×g for 5 min. The remaining culture was pelleted at the same speed, washed in H-Leu medium and resuspended in H-Leu medium with 2% galactose to induce the expression of PAP and PAPx. At various times during induction (2, 4, 8, 12 and 24 h), aliquot were removed, pelleted and stored at −80° C. Pellets for ribosome isolation were washed twice in water and quickly frozen in liquid $N_2$.

Ribonuclease protection assay. RNA from frozen yeast aliquot was extracted according to Cui et al., EMBO J. 15:5726–5736 (1996). Total RNA from the time point aliquot of PAP and PAPx induced in mak8-1 cells was used in the RNase protection assay as described in Turner, et al., J. Virol. 72:1036–1042 (1998).

Protein expression analysis. Frozen pellets of 2 ml aliquot of cells harvested during the time course induction of PAP and PAPx were resuspended in an equal volume of cold (4° C.) phosphate buffered saline (PBS) buffer and 0.3 g of 0.5 mm diameter glass beads. Cells were vortexed for 2 min and centrifuged at 16,000×g for 5 min. Supernatant total protein was quantified by Bradford using BSA as a standard. Total protein (30 μg) from each time point was separated through 12% SDS-PAGE, transferred to nitrocellulose, and probed with either an affinity purified (Lindstrom, et al., Plant Physiol. 106:7–16 (1994)) polyclonal antibody to PAP (1:5000) or a monoclonal antibody to L3 (anti TCM 7.1.1, gift of J. R. Warner) (1:5000). PAP and L3 were visualized by chemiluminescence using a Renaissance kit (NEN, Du Pont). To probe proteins with two separate antibodies, blots were stripped by incubation in 8M guanidine hydrochloride at room temperature for 30 min. The nitrocellulose was washed four times in PBST for 15 min each before exposing the blot to another antibody.

Isolation of Yeast Ribosomes

Yeast cells harvested from 25 ml aliquot during the time course induction of PAP and PAPx in wild-type and mak8-1 cells were ground to a fine powder in liquid $N_2$ with a mortar and pestle. Cold (4° C.) buffer A [4 ml of 200 mM Tris-HCl pH 9.0, 200 mM KCl, 200 mM sucrose, 25 mM $MgCl_2$, 25 mM EGTA, 25 mM 2-mercaptoethanol] was added to the yeast powder and centrifuged at 16,000×g for 20 min. The resulting supernatant was increased to 13 ml with buffer A and layered over a 10 ml cushion of 1 M sucrose, 25 mM Tris-HCl pH 7.6, 25 mM KCl, 5 mM $MgCl_2$. Ribosomes were pelleted by centrifugation at 311,000×g for 3.5 h at 4° C. The pellets were resuspended in 100 μl of 25 mM Tris-HCl pH 7.6, 25 mM KCl, 5 mM $MgCl_2$, aliquoted and stored at −80° C.

rRNA Depurination Assay

Total ribosomes (50 μg) isolated from yeast cells expressing PAP, PAPx or vector control were resuspended in RIP buffer [167 mM KCl, 100 mM Tris-HCl pH 7.2, 100 mM $MgCl_2$] to a final volume of 100 μl. Extraction of rRNA and subsequent analysis for depurination were conducted according to Tumer, et al., Proc. Natl. Acad. Sci. USA 94:3866–3871 (1997). A positive control standard for depurination was generated by incubating 50 μg of ribosomes from wild-type yeast with 100 ng of purified PAP (Calbiochem) in RIP buffer. The mixture was incubated at 37° C. for 30 min and RNA isolated as referenced above. Depurination of rRNA was confirmed by the presence of a 360 nt fragment visible on the urea-acrylamide gel.

Co-Immunoprecipitation

PAP and L3 expressed in vivo in wild-type and mak8-1 cells were co-immunoprecipitated with the monoclonal antibody to L3 essentially as described in Otto, et al., Meth. Cell Biol. 37:119–126 (1993). Ribosomes (100 μg) from cells induced to express PAP, PAPx or vector control were used as substrate for immunoprecipitation with protein A-Sepharose beads. The pelleted complex of antibody and protein was eluted from the beads with SDS sample buffer and visualized by immunoblot analysis using the antibodies to PAP and L3. Co-immunoprecipitation of in vitro synthesized L3 with purified PAP was used to demonstrate a direct interaction between these two proteins. Radiolabeled L3 (3 nM), synthesized by a linked transcription translation system (TNT Coupled Reticulocyte Lysate System (Promega)) was incubated with 3 nM purified non-radiolabeled PAP and immunoprecipitated with the monoclonal L3 antibody. Proteins were eluted from the Sepharose beads with SDS sample buffer and the solution divided in half. Half was separated through 12% SDS-PAGE, transferred to nitrocellulose and probed with the polyclonal antibody to PAP. The remaining half was also separated through 12% SDS-PAGE, then incubated with Entensify Solution A and B (NEN, Du Pont), dried and exposed to autoradiography.

Results

Mak8-1 Cells are Resistant to PAP

PAP removes a specific adenine residue from the α-sarcin loop of yeast 25S rRNA. Since this loop is located near the peptidyltransferase center, PAP was introduced into the strain harboring the mak8-1 allele to determine if this mutation conferred resistance to the cytostatic effects of PAP. Both wild type and mak8-1 cells were transformed with the LEU2-based vector, pNT188, containing the PAP cDNA under the control of a GAL1 promoter. Galactose induction of PAP expression did not have a cytostatic effect on the growth of the strain harboring the mak8-1 allele (photograph not shown). In contrast, growth of wild-type cells was significantly inhibited when PAP expression was induced by galactose. To confirm this observation, isogenic RPL3::hisG strains (Peltz, et al., infra) were tested for their sensitivity to PAP. Cells harboring pmak8-1 were able to grow under PAP induction, whereas cells containing pRPL3 encoding wild type L3 did not grow (data not shown).

PAP is expressed in mak8-1 cells. Resistance to PAP may have arisen because either transcript or protein had not accumulated in mak8-1 cells. To determine if PAP transcripts were synthesized, nuclease protection assays were performed to examine the accumulation of PAP mRNA relative to CYH2 mRNA, an internal control which encodes the ribosomal protein L29 (Stocklein, et al., Curr. Genet. 1:177–183)). The levels of PAP transcript were compared to those of PAPx, the active site mutant of PAP. The zero hour time point represents cells grown in raffinose under non-inducing conditions. Cells grown in raffinose did not express PAP or PAPx transcripts (photograph not shown). However, two hours after shifting to galactose-containing medium, transcripts corresponding to both PAP and PAPx were detected in mak8-1 cells. Quantitation of PAP mRNA, relative to the CYH2 internal control, indicated that both PAP and PAPx transcript levels remained constant during the time course of induction. A protected RNA fragment corresponding to PAP was not observed in cells containing the vector alone, eight hours after induction by galactose (photograph not shown). When tRNA was used in place of total cellular RNA as a control, no specific binding by the radiolabeled probes was detected (photograph not shown). These results demonstrated that both PAP and PAPx mRNAs were transcribed in cells harboring the mak8-1 allele and no significant difference in the level of transcripts could be detected in cells expressing PAP or PAPx.

To test whether PAP was expressed and accumulated in mak8-1 cells, immunoblot analysis was conducted on aliquots harvested from cells grown on galactose medium through a 24 hour time course. The same experiment was carried out with wild-type yeast cells harboring PAP (NT188) and PAPx (NT224). Similar amounts of PAP and PAPx were expressed in mak8-1 cells, suggesting a lack of toxicity due to PAP accumulation, whereas in wild type cells, PAPx was expressed to a greater degree than PAP (photograph not shown). The higher molecular mass protein reacting with the PAP antibody likely represents the precursor form of PAP, observed previously in yeast (Hur, et al, supra). Over-expression of PAPx often results in lower molecular mass proteins, most likely breakdown products, seen clearly in wild-type cells induced for 24 h. However, the primary band in each immunoblot is the 29 kDa mature form of PAP.

Mak8-1 Ribosomes are not Depurinated by PAP

To determine whether there were differences between the ability of PAP to depurinate ribosomes from wild-type and mak8-1 cells in vivo, ribosomes were isolated from yeast cells induced to express PAP or PAPx for 8 hours. rRNA was isolated from these ribosomes, treated with aniline and separated on a urea-acrylamide gel. Depurination of rRNA was revealed by the presence of the 360-nucleotide (nt) fragment produced by removal of a purine residue from the 25S rRNA and subsequent cleavage at that site by treatment with aniline. A positive standard for depurination was generated by incubating wild-type ribosomes with PAP in vitro, extracting the rRNA and treating it with aniline (photograph not shown). Ribosomes isolated from wild-type cells harvested 8 hours after induction of PAP expression were depurinated, whereas ribosomes of cells harboring the mak8-1 allele were not depurinated during PAP expression in vivo (photograph not shown). Ribosomes isolated from both cell types expressing PAPx were not depurinated, which was consistent with the prior observation that PAPx lacks enzymatic activity.

PAP Does not Associate with Ribosomes in mak8-1 Cells

A possible reason for the lack of depurination of rRNA in mak8-1 cells was that PAP might not be able to access its rRNA substrate in these cells. To determine if PAP associated with ribosomes in wild-type cells, ribosomes examined for depurination were also assessed by immunoblot analysis with the affinity-purified antibody against PAP. Both PAP and PAPx were associated with ribosomes in wild-type cells (photograph not shown). In contrast, neither PAP nor PAPx could be detected with ribosomes isolated from mak8-1 cells. The higher levels of PAPx associated with ribosomes of wild-type cells likely reflected the increased level of expression of enzymatically inactive PAPx relative to the enzymatically active PAP (photograph not shown). The immunoblots of ribosomal proteins were stripped and re-probed with a monoclonal antibody against L3 to illustrate that L3 or its mutant form were detected on both types of ribosomes and that similar amounts of protein were loaded from both cell types (photograph not shown).

PAP Binds Free L3 and Mak8-1p

Results described above indicated that PAP is associated with ribosomes in wild-type cells, but not in mak8-1 cells, suggesting that PAP may interact with L3. To test the hypothesis of direct interaction with L3, purified PAP was mixed with in vitro synthesized L3 or Mak8-1p and co-immunoprecipitated with the monoclonal L3 antibody. Purified PAP co-immunoprecipitated with L3 or Mak8-1p when it was mixed with either protein and not when it was incubated alone (photograph not shown). As expected, L3 and Mak8-1p were immunoprecipitated with L3 antibody when they were each mixed with PAP or incubated alone (photograph not shown). These results indicate that PAP binds directly to L3 or Mak8-1p in its free form (photograph not shown).

Co-Immunoprecipitation of PAP and L3 from Ribosomes

To determine if PAP interacts with L3 and Mak8-1p incorporated into ribosomes, ribosomes from wild-type or mak8-1 cells expressing either PAP, PAPx or vector alone were immunoprecipitated with the monoclonal L3 antibody. PAPx was co-immunoprecipitated with L3 from ribosomes of wild-type but not mak8-1 cells indicating that PAPx does not interact with the mutant form of L3 in ribosomes (photograph not shown). The lack of co-immunoprecipitation of PAP with L3 from ribosomes of wild-type cells may reflect the previous observation that wild-type protein is not synthesized as abundantly as the active site mutant (photograph not shown). The difference may also be the result of variation in the kinetics of association between PAP and PAPx, namely PAP may dissociate more readily from its substrate, the ribosomes, than PAPx. The results demonstrate that L3 or Mak8-1p was immunoprecipitated from ribosomes of both cell types and that similar amounts of protein were loaded on the gel. These results suggest that the absence of association between PAP and Mak8-1p in ribosomes may be the result of a conformational change, such that the peptide sequence or tertiary structure required is not accessible when Mak8-1p is incorporated into ribosomes. The lack of co-immunoprecipitation of PAP with Mak8-1p in ribosomes substantiates earlier results that showed absence of PAP in ribosomes from mak8-1 cells and lack of rRNA depurination.

A previous report is that in vivo induction of PAP expression in yeast had a cytostatic effect (Hur, et al., supra). The work described herein demonstrates that cells containing the mak8-1 allele are resistant to PAP. The lack of growth inhibition observed in mak8-1 cells is believed to be due to the fact that ribosomes from these cells are not associated with PAP, and consequently are not depurinated. The observation that PAP expressed in wild-type yeast depurinates ribosomes, but does not when expressed in mak8-1 cells, indicates that wild-type L3 is required for depurination of ribosomes. Co-immunoprecipitation experiments with isolated proteins illustrates that PAP directly binds to L3 and Mak8-1p in vitro. However, when the experiments were repeated using intact ribosomes, PAP co-immunoprecipitated only with wild-type L3 from ribosomes and not with Mak8-1p, indicating that PAP does not interact with Mak8-1p in ribosomes. The quaternary structure of a ribosome containing Mak8-1p may differ from a wild-type ribosome, such that the binding site for PAP may be masked in the mutant ribosomes. Alternatively, a difference in post-translational modifications between L3 and Mak8-1p may affect its interaction with PAP in vivo. The hypothesis for altered binding by the mutant L3 is supported by the observation that neither PAP nor PAPx was dectected in association with ribosomes in mak8-1 cells even though both proteins were associated with ribosomes in wild-type cells.

This evidence demonstrates a link between L3 and the a-sarcin loop in eukaryotic ribosomes. Experiments designed to reconstitute the minimal ribosomal particle still capable of enzyme activity have established that L3 is essential for maintaining peptidyltransferase activity (Hampl, et al., J. Biol. Chem. 256:2284–2288 (1981)). A photolabile cDNA probe targeted to the central loop of domain V was shown to cross-link to L3 (Alexander, et al., Biochem. 33:12109–12118 (1994)). With the use of a photolabile oligodeoxynucleotide probe complementary to the a-sarcin region of E. coli, Muralikrishna, et al., (Nucleic Acids Res. 25:4562–4569 (1997)) recently demonstrated the proximity of the a-sarcin region to domains IV and V of E. coli rRNA. tRNA localization experiments further demonstrated the mutual proximity of domains IV, V and VI within the 50S subunit (Joseph, et al., EMBO J. 15:910–916 (1996)). Chemical and enzymatic footprinting have shown that L3 binds in region VIA of 23S rRNA near the a-sarcin loop (Muralikrishna, et al., Biochem. 30:5421–5428 (1991)). The results described herein substantiate prior data (not shown) that both PAP and PAPx bind to the a-sarcin loop because they suggest that L3 is in close proximity of the a-sarcin loop in yeast 25SrRNA.

These data lead us to propose a model to explain the interaction between PAP and L3. Co immunoprecipitation studies demonstrate that PAP binding to ribosomes requires wild-type L3. Therefore, we suggest that PAP accesses its substrate, the a-sarcin loop, by recognizing and binding to L3. Once bound, the close proximity of L3 to the a-sarcin loop facilitates the subsequent depurination of the 25S rRNA by PAP. Since PAPx does not interact with ribosomes from mak8-1 cells, we contend that the PAP binding site may be masked in mak8-1 ribosomes. The mak8-1 gene product encodes a mutant L3 that differs from the wild-type by only two amino acid substitutions, W255C and P257S, which may be sufficient to alter the shape of the protein product (Peltz, et al., infra), affecting its interaction with other components of the ribosome. If rRNA is necessary to place the ribosomal proteins in a proper conformation to facilitate PAP binding, the point mutations in Mak8-1p may alter the interaction between rRNA and Mak8-1p.

While the mechanism underlying the catalytic activity of RIPs is understood, very little is known about how RIPs gain access to the ribosome. Although all RIPs have the same specificity for adenine 4324 of naked 28S rRNA, they show very different levels of activity against ribosomes of different species. For example, ricin is 23,000 times more active on rat liver ribosomes than on plant ribosomes (Harley, et al., Proc. Natl. Acad. Sci. USA 79:5935–5938 (1982)), while PAP is equally active on ribosomes from all five kingdoms. These data suggest that the differences in sensitivity of ribosomes to RIPs may reflect differences in interactions of RIPs with ribosomal proteins. Endo and Tsurugi (Endo, et al., J. Biol. Chem. 263:8735–8739 (1988)) showed that the ricin A-chain depurinated rat rRNA at adenine 4324 in intact ribosomes much more efficiently than naked 28S rRNA. Conversely, the ricin A-chain depurinated naked 23S rRNA of E. coli at the homologous adenine 2660, and did not depurinate intact E. coli ribosomes. Formation of a covalent complex between saporin and a component of the 60S subunit of yeast ribosomes was shown by chemical cross-linking (Ippoliti, et al., FEBS Lett. 298:145–148 (1992)). Similarly, the ricin A-chain has been cross-linked to mammalian ribosomal proteins L9 and L10e (Vater, et al., J. Biol. Chem. 270:12933–12940 (1995)). Despite some evidence for the dependence of RIP activity on the type of ribosomal substrate, the functional significance of the association between RIPs and ribosomal proteins has not been reported. Nevertheless, these observations support the hypothesis for a molecular recognition mechanism involving one or more ribosomal proteins that could provide receptor sites for toxins and favor optimal binding to the target adenine. The results reported here demonstrate that PAP gains access to the ribosome by recognizing L3. Since L3 is highly conserved among ribosomes from different species, the interaction between PAP and L3 may be the underlying reason for the broad-spectrum activity of PAP on ribosomes from different organisms.

The text of Example 1 is contained in Hudak, et al., J. Biol. Chem. 274:3859–3864 (1999).

EXAMPLE 2

Ribosomal Protein L3 Mutants Alter Translational Fidelity and Promote Rapid Loss of the Yeast Killer Virus Programmed −1 ribosomal frameshifting is utilized by a number of RNA viruses as a means to ensure the correct ratio of viral structural to enzymatic proteins available for viral particle assembly. Altering frameshifting efficiencies upsets this ratio, interfering with virus propagation. We have previously demonstrated that compounds that alter the kinetics of the peptidyl-transfer reaction affect programmed −1 ribosomal frameshift efficiencies and interfere with viral propagation in yeast. Here, the use of a genetic approach lends further support to the hypothesis that alterations affecting the ribosome's peptidyl-transferase activity lead to changes in frameshifting efficiency and virus loss. Mutations in the RPL3 gene, which encodes a ribosomal protein located at the peptidyl-transferase center, promote approximately 3- to 4-fold increases in programmed −1 ribosomal frameshift efficiencies and loss of the $M_1$ killer virus of yeast. The mak8-1 allele of RPL3 contains two adjacent missense mutations which are predicted to structurally alter the Mak8-1p. These results support the hypothesis that alterations in the peptidyl-transferase center affect programmed −1 ribosomal frameshifting.

Introduction

Programmed −1 ribosomal frameshifting is a mode of regulating gene expression used predominantly by RNA viruses and by a subset of bacterial genes to induce elongating ribosomes to shift reading frame in response to specific mRNA signals (reviewed in 16,24,27,30). Many viruses of clinical, veterinary and agricultural importance utilize programmed frameshifting for the production of their structural and enzymatic gene products (reviewed in 5,6,24, 27,30,51). Thus, ribosomal frameshifting is a unique target to identify and develop antiviral agents (20,41). Programmed −1 ribosomal frameshifting causes the ribosome to slip one base in the 5' direction and requires two cis-acting mRNA signals. The first sequence element is called the 'slippery site' which, in eukaryotic viruses, consists of a heptamer sequence spanning three amino acid codons X XXY YYZ (the gag reading frame is indicated by spaces), where XXX can be any three identical nucleotides, YYY can be AAA or UUU, and Z is A, U, or C (8,17,21,31). The second frameshift-promoting signal is usually a sequence that forms a defined RNA secondary structure, such as an RNA pseudoknot (7,17,36).

A 'simultaneous slippage model' has been proposed to explain how ribosomes can be induced to change reading frames (31). A translating ribosome in which the A- and P-sites are occupied by tRNAs is forced to pause over the slippery site as a consequence of the RNA pseudoknot. The increased pause time over this sequence is thought to give an opportunity for the ribosome and bound tRNAs to slip one base in the 5' direction. Because of the nature of the slippery site, this still leaves their non-wobble bases correctly paired with the mRNA in the new reading frame. Following the slip in the −1 direction, the ribosome continues translation in the new reading frame, producing the Gag-pol polyprotein. In the yeast Saccharomyces cerevisiae the L-A dsRNA virus utilizes a −1 ribosomal frameshift event for the production of a Gag-Pol fusion protein and has been an excellent model system to investigate this process (reviewed in 12,20). $M_1$, a satellite dsRNA virus of L-A that encodes a secreted killer toxin, is encapsidated and replicated using the Gag and Gag-pol gene products synthesized by the L-A virus (reviewed in 58). Maintaining the appropriate ratio of Gag to Gag-Pol is critical for maintenance of the $M_1$ virus (21). Alteration of the frameshift process by as little as 2- to 3-fold promotes rapid loss of $M_1$ (21,22). Compounds that bind to the peptidyl transferase center on the ribosome and reduce translation fidelity can also modulate ribosomal frameshifting (19). Anisomycin and sparsomycin were shown to alter programmed −1 ribosomal frameshifting efficiencies both in cells and in in vitro translation extracts and to promote loss of the yeast L-A and its satellite dsRNA virus, $M_1$ (19). These results indicate that modulating the ribosomal peptidyl transferase center can alter the efficiency of programmed −1 ribosomal frameshifting and lead to inefficient virus propagation.

In the current study we have genetically investigated the role of a ribosomal protein that is located at the ribosomal peptidyl transfer center in modulating programmed frameshifting efficiencies. Previous results have shown that the yeast RPL3 gene encoding the ribosomal protein L3 participates in the formation of the peptidyl transferase center (reviewed in 38,39). Mutations in the RPL3 gene (called TCM1) were initially identified by conferring resistance to the peptidyl-transferase inhibitors trichodermin and anisomycin (32,45). Independently, the MAK8 gene (MAK=MAintenance of Killer) was identified by the inability of mutant alleles to maintain the $M_1$ satellite virus (59). Subsequent analysis demonstrated that MAK8 is allelic to RPL3 (60). Thus, a mutation in a ribosomal protein located in the peptidyl-transferase center that cannot maintain the killer virus has been identified. We hypothesized that the underlying cause of killer virus loss observed in these cells may be a consequence of increased programmed −1 ribosomal frameshifting efficiency, i.e. that the mak8 alleles may demonstrate a Mof phenotype. The results presented here demonstrate that strains harboring the mak8-1 allele have increased programmed frameshifting efficiencies and strongly suggest that the loss of the killer virus is a due to alteration in translation fidelity. These results support the notion that modulating the peptidyl-transferase center results in alteration of programmed −1 ribosomal frameshifting efficiencies, promoting loss of the killer virus.

Materials and Methods

Strains, Media, Enzymes, Oligonucleotides, and Drugs

E. coli DH5α and MV1190 were used to amplify plasmid DNA. The yeast strains used in this study are listed in Table 1. Transformation of yeast and E. coli were performed as described previously (13). YPAD, YPG, SD, synthetic complete medium (H-) and 4.7 MB plates for testing the killer phenotype were as previously reported (22). Restriction enzymes were obtained from Promega, MBI Fermentas, BRL and Boehringer Mannheim. T4 DNA ligase and T4 DNA polymerase were obtained from Boehringer Mannheim, and precision Taq polymerase was obtained from Stratagene. Radioactive nucleotides were obtained from NEN. Oligonucleotides used in these studies were purchased from IDT, and DNA sequence analysis was performed by the UMDNJ-RWJ DNA synthesis center. Anisomycin was purchased from Sigma, and sparsomycin was a generous gift from Dr. S. Pestka.

Plasmid Constructs and Programmed Ribosomal Frameshift Assays

BlueScript KS plasmid was obtained from Strategene. The pRS series of plasmids (10,47) and pAS134 (1) have been previously described. Full length RPL3 and mak8-1 were amplified from genomic DNA by polymerase chain reaction using the oligonucleotide primers −300 Kpn I (5' CCCCGGTACCTCACGCACACTGGAATGAAT 3') (SEQ ID NO: 13) and +1300 Sac I (5' CCCCGAGCGCAACCTC-CATTTTGGACTTGG 3') SEQ ID NO: 14), and were cloned into the pRS300 series (pRS314, pRS315 and pRS316) digested with Kpn I and Sac I to make the pRPL3 and the pmak8-1 series of plasmids. To construct a RPL3 gene disruption plasmid, the Kpn I/Sac I RPL3 clone was subcloned into BlueScript KS (KS-RPL3), digested with Sph I, the overhanging ends were filled with dNTPs using T4 DNA polymerase, and was then digested with Xba I. Subsequently, pAS134 was digested with Xba I and Pvu II to liberate the hisG-UPA3 cassette which was subcloned into the Xba I/blunt ended KS-RPL3 to create pJD168.

Construction of Isogenic mak8-1 and RPL3 Strains

Yeast strains JD100 and JD973 were mated, the diploids transformed with Pvu II-linearized pJD168, and selected on H-Ura medium (22). Disruption of the RPL3 locus on one chromosome was confirmed by Southern analysis as described below. Diploids were selected for loss of the chromosomal URA3 insert by growth on 5-flouroorotic acid (5-FOA). Ura-cells were transformed with pRPL3-Ura3, sporulated, and dissected onto YPAD medium. The resulting tetrads are from cross JD980. rpl3Δ status was confirmed by the inability of spore clones to grow in the presence of 5-FOA. To construct isogenic mak8-1 strains, cells were transformed with pmak8-1-TRP1, and were subsequently grown in the presence of 5-FOA to select for loss of the wild-type pRPL3-Ura3 plasmid.

Killer Assay

The killer virus assay was carried out as previously described (21). Briefly, yeast colonies were replica plated to 4.7 MB plates (22) with a newly seeded lawn of strain 5×47 (0.5 ml of a suspension at 1 unit of optical density at 550 nm per ml per plate). After 2–3 days at 20° C., killer activity was observed as a clear zone around the killer colonies. Loss-of-killer assays were performed in multiple wild-type and mutant strains.

Nucleic Acids Analyses

DsRNAs of L-A and $M_1$ viruses were prepared as described (25), separated by electrophoresis through 1.2% agarose gels, denatured in the gels in two changes of 30 min each of 50% formamide, 9.25% formaldehyde-1× Tris-acetate-EDTA at room temperature and transferred to nitrocellulose in 20×SSC. L-A and $M_1$ (−) strand RNA probes were labeled with [α-$^{32}$P]UTP and hybridized to blots and washed as described in (22). RNase protection assays to determine the relative abundances of the lacZ −1 frameshift reporter mRNAs and U3 small nuclear RNA (snRNA) in isogenic wild-type, mak8-1 and L3Δ strains were carried out as described (44).

Results

The mak8-1 Allele of RPL3 Promotes Increased Programmed −1 Ribosomal Frameshifting Efficiencies Previous studies have demonstrated that peptidyl-transferase inhibitors specifically affect programmed −1 ribosomal frameshifting efficiencies (19). Thus, we predicted that yeast strains harboring chromosomal mutations affecting the peptidyl-transferase center would also have defects in programmed −1 ribosomal frameshifting and killer virus maintenance. The mak8-1 allele of ribosomal protein L3 initially presents a logical candidate to test this hypothesis, since strains harboring this mutation promoted loss of the killer virus. Programmed ribosomal frameshifting efficiencies were measured in vivo using a series of lacZ reporter plasmids as described previously (12,17,19,54). The efficiencies of −1 and +1 ribosomal frameshifting are calculated by determining the ratio of beta-gal activities measured in cells harboring p−1 or p+1 to those harboring p0, and multiplying by 100%.

After cells (strain 1906; Table 1) harboring the mak8-1 allele were transformed with p0, p−1, or p+1 the efficiencies of programmed ribosomal frameshifting were determined. The results demonstrated that the programmed −1 frameshifting efficiency in the mak8-1 strain was 5.2%, approximately 3-fold greater than the 1.7%–2.0% normally observed in wild-type strains (Table 2). To confirm that the change in programmed −1 ribosomal frameshifting efficiency was solely due to the mak8-1 allele, isogenic wild-type and mak8-1 strains were constructed and programmed −1 frameshifting was determined in these cells as described above (cross JD980; Table 1). In isogenic backgrounds, the mak8-1 allele of RPL3 promotes an approximately 2.5-fold increase in programmed −1 ribosomal frameshift efficiency (≈4.9% in mak8-1 compared to =1.9% in the isogenic wild-type strain; Table 2). The mak8-1 allele was also unable to maintain the $M_1$ killer virus (Table 2). However, mak8-1 had no effect on programmed +1 ribosomal frameshifting (Table 2). Taken together, these results demonstrate that the mak8-1 allele causes an alteration in programmed −1 ribosomal frameshift efficiencies. Thus, the mak8-1 allele is also a mof mutant, in that these strains demonstrate increased programmed −1 ribosomal frameshifting efficiencies and loss of the killer virus (11,12).

Characterization of the mak8-1 Lesion

The mak8-1 allele was amplified by PCR from genomic DNA harvested from strain 1906 and the DNA sequence was obtained from three independently isolated clones (see Materials and Methods). The results demonstrated that the mak8-1 allele harbors two separate mutations spaced four nucleotides apart. The G765C mutation encodes a Trp-to-Cys change at amino acid residue 255. The C769T mutation changes a proline at residue 257 to serine, a potentially significant structural change.

Strains Harboring the mak8-1 Allele are Resistant to the Effects of Peptidyl-Transferase Inhibitors on Programmed −1 Ribosomal Frameshifting We previously demonstrated that peptidyl-transferase inhibitors specifically alter programmed −1 ribosomal frameshifting efficiencies (19). It has been previously demonstrated that cells harboring mutant alleles of rpl3 are resistant to the cytotoxic effects of peptidyl-transferase inhibitors (28,32,45,60). These include strains harboring the mak8 and the tcm1 classes of RPL3 alleles. Thus, we asked whether this class of agents affect programmed −1 ribosomal frameshifting in strains harboring the mak8-1. To examine this, mak8-1 and wild-type cells harboring either p0 or p−1 frameshift indicator plasmids were grown in the presence of various concentrations of either anisomycin or sparsomycin for four hours and programmed ribosomal frameshifting efficiencies were determined as described above. The results demonstrated that both anisomycin and sparsomycin altered ribosomal frameshifting in wild-type cells (Figures not shown). In contrast, neither anisomycin nor sparsomycin had any further effect on programmed −1 ribosomal frameshifting in mak8-1 strains (Figures not shown). These results provide strong evidence that a defect affecting the peptidyl-transferase center is responsible for the observed increase in programmed −1 ribosomal frameshifting in mak8-1 cells.

Discussion

Mutations Affecting Ribosomal Protein L3 Promote Loss of the $M_1$ Killer Virus by Altering the Efficiency of Programmed −1 Ribosomal Frameshifting The mechanism governing programmed −1 ribosomal frameshifting suggests that drugs and mutations which affect the peptidyl-transfer reaction may alter programmed −1 ribosomal frameshift efficiencies and have antiviral effects (19). We previously used peptidyl-transferase inhibitors to demonstrate the validity of this model (19). The results presented here have shown that an allele encoding a mutant form of ribosomal protein L3, which was previously implicated in formation of the peptidyl-transferase center, also alters programmed −1 ribosomal frameshift efficiencies and has antiviral effects. These results support the hypothesis that the peptidyl-transferase center may present a novel target for anti-retroviral therapeutic agents.

It has long been known that cells harboring mak8 alleles cannot propagate the $M_1$ satellite virus (59). Additional alleles of RPL3, named tcm1, were also characterized based on their resistance to the peptidyl-transferase inhibitor trichodermin (26,28,32,45,46). These alleles also have the Mak⁻ phenotype (60). However, the precise mechanism responsible for killer virus loss in this class of mutants was not determined. The results presented here demonstrate that alterations in programmed −1 ribosomal frameshifting efficiencies are responsible for the inability cells harboring this mutation to maintain the $M_1$ dsRNA virus. Given the previous demonstration that peptidyl-transferase inhibitors promote virus loss by altering programmed −1 ribosomal frameshift efficiencies, as well as the role of the L3 protein in peptidyl-transferase center formation, our results indicating that mutations in RPL3 affect programmed −1 ribosomal frameshifting are consistent with the view that altering peptidyl transfer activity affects this process.

We envision two models to explain the role of the L3 protein in programmed −1 ribosomal frameshifting. In one, we suggest that the incorporation of defective L3 protein (Mak8-1p) into ribosomes would result in suboptimal L3 function, yielding the observed translational fidelity defect. Alternatively, it is possible that expression of this allele results in a subpopulation of L3-deficient ribosomes. Since it is thought that the large rRNA is responsible for peptidyl-transferase activity (38,61), these L3-deficient ribosomes would retain a small amount of peptidyl-transferase activity. In both scenarios, defects in peptidyl-transferase activity are predicted to slow the rate of translation elongation while both the ribosomal A- and P-sites are occupied. In the context of frameshifting, this would result in a longer ribosomal pause at the programmed −1 ribosomal frameshift signal, increasing the likelihood of a successful frameshift. If this model is true, then the observed increases in programmed −1 ribosomal frameshifting efficiencies promoted by these alleles should represent the sum of programmed frameshifting promoted by normal plus defective ribosomes.

REFERENCES

1. Alani, et al., Genetics 116:541–545 (1987).
2. Anderson, et al., EMBO J. 17:1497–1506 (1998).
3. Balasundaram, et al., Proc. Natl. Acad. Sci. USA 91:172–176 (1994).
4. Benard, et al., Mol. Cell. Biol. 18:2688–2696 (1998).
5. Bishop, et al., Annu. Rev. Biochem. 47:35–88 (1978).
6. Brierley, et al., J. Gen. Virol. 76:1885–1892 (1995).
7. Brierley, et al., Cell 57:537–547 (1989).
8. Brierley, J. Mol. Biol. 227:463–479 (1992).
9. Bruenn, et al., Nucleic Acids Research 3:2427–436 (1976).
10. Christianson, et al., 1992. Yeast 110:119–122 (1992).
11. Cui, et al., Mol. Cell. Biol. 18:1506–1516 (1998).
12. Cui, et al., EMBO J. 15:5726–5736 (1996).
13. Cui, et al., Genes & Dev. 9:423–436 (1995).
14. Cui, et al., Mol. Cell. Biol (1998).
15. Czaplinski, et al., Genes & Dev. 12:1665–1667 (1998).
16. Dinman, et al., Yeast 11:1115–1127 (1995).
17. Dinman, et al., Proc. Natl. Acad. Sci. USA 88:174–178 (1991).
18. Dinman, et al., RNA 3:870–881 (1997).
19. Dinman, et al., Proc. Natl. Acad. Sci. USA 94:6606–6611 (1997).
20. Dinman, et al., Trends in Biotech. 16:190–196 (1998).
21. Dinman, et al., J. Virology 66:3669–3676 (1992).
22. Dinman, et al., Genetics 136:75–86 (1994).
23. Dinman, et al., Genetics 141:95–105 (1995).
24. Farabaugh, et al., Microbiol. Rev. 60:103–134 (1996).
25. Fried, et al., Proc. Natl. Acad. Sci. USA 75:4224–4228 (1978).
26. Fried, et al., Proc. Natl. Acad. Sci. USA 78:238–242 (1981).
27. Gesteland, et al., Annu. Rev. Biochem. 65:741–768 (1996).
28. Grant, et al., Genetics 83:667–673 (1976).
29. Hsu, et al., Molecular & Cellular Biology 13:4826–4835 (1993).
30. Jacks, et al., Curr. Top. Microbiol. Immunol. 157:93–124 (1996).
31. Jacks, et al., Cell 55:447–458 (1998).
32. Jimenez, et al., Biochim. Biophys. Acta 383:427–434 (1975).
33. Johnson, et al., Molecular & Cellular Biology 15:2719–2727 (1995).
34. Lee, et al., Proc. Natl. Acad. Sci. USA 92:6587–6591 (1995).
35. Masison, et al., Mol. Cell. Biol. 15:2763–2771 (1995).
36. Morikawa, et al., Virology 186:389–397 (1992).
37. Muhlrad, et al., Genes & Dev. 6:2100–2111 (1992).
38. Noller, et al., J. Bacteriol. 175:5297–5300 (1993).
39. Noller, et al., Annu. Rev. Biochem. 66:679–716 (1997).
40. Ohtake, et al., Mol. Cell. Biol. 15:2772–2781 (1995).
41. Peltz, et al., "Identification of the cis-acting sequences and trans-acting factors involved in nonsense-mediated mRNA decay," p. 1–10. In Tuite, et al., (eds.), *Protein synthesis and targeting in yeast.* Springer-Verlag (1993).
42. Ridley, et al., Molecular & Cellular Biology 4:761–770 (1984).
43. Ruiz, et al., EMBO J. 17:575–589 (1998).
44. Ruiz, et al., Proc. Natl. Acad. Sci. USA 95:8721–8726 (1998).
45. Schindler, et al., Nature 248:535–536 (1974).
46. Schultz, et al., J. Bacteriol. 155:8–14 (1983).
47. Sikorski, et al., Genetics 122:19–27 (1989).
48. Somogyi, et al., Mol. Cell. Biol. 13:6931–6940 (1993).
49. Stevens, et al., J. Biol. Chem. 255:3080–3085 (1980).
50. Stevens, et al., Archives of Biochemistry & Biophysics 252:339–347 (1987).
51. TenDam, et al., Virus Genes 4:121–136 (1990).
52. Thiele, et al., Virology 137:2031 (1984).
53. Tu, et al., Proc. Natl. Acad. Sci. USA 89:8636–8640 (1992).
54. Turner, et al., J. Virol. 72:1036–1042 (1998).
55. Weng, et al., Mol. Cell. Biol. 16:5491–5506 (1996).
56. Weng, et al., Mol. Cell. Biochem. 16:5477–5490 (1996).
57. Weng, et al., RNA 4:205–214 (1998).
58. Wickner, et al., Microbiol. Rev. 60:250–265 (1996).
59. Wickner, et al., Genetics 76:423–432 (1974).
60. Wickner, et al., Proc. Natl. Acad. Sci. USA 79:4706–4708 (1982).
61. Zhang, et al., Nature 390:96–100 (1997).

TABLE 1

Yeast Strains used in this study

| Strain | Genotype | Source |
|---|---|---|
| 1906 | MATa leu2 mak8-1 K$^-$ MKT$^+$ | R. Wickner |
| 5X47 | MATa/MATα his1/+ trp1/+ ura3/+ K$^-$R$^-$ | " |
| 2373 | MATa ura3 ski4-1 mkt1 K$^{++}$ | " |
| 2898 | MATa ura3 ade3 his(5, 6) ski6-2 K$^{++}$ | " |
| 2413 | MATa ura3 cyh2 ski7-2 K$^{++}$ | " |
| JD100 | MATa ura3-52 his3 trp1-δ1 K1$^+$ | This study |
| JD973 | MATα ura3-SK1 LEU2::hisG TRP1::hisG lys2-SK1 ho::LYS2 ade3-210S | " |
| Cross JD980 | JD100 X JD973 with RPL3::hisG on one chromosome | " |
| JD980-10C | MATα lys2 his3 ura3 LEU2::hisG trp1-δ1 RPL3::hisG + pRPL3 or pmak8-1. | " |
| JD13 | MATa his3 leu2 PEP4::HIS3 NUC1::LEU2 ura3 K1$^+$ | " |
| JD111 | MATα ura3-52 lys2-801 trp1-δ1 leu2$^-$ his3$^-$ K1$^+$ | " |
| JD890 | MATα ura3-52 trp1 leu2Δ1 his3Δ300 pbrΔ1-6 can1$^r$ pep4::HIS3 SKI1::LEU2 [L-AHN M$_1$] K$^{++}$ | " |
| JD2 | MATα ura3 trp1 ade8 ski2-2 K$^{++}$ | " |

TABLE 2

| Strain | $^a$% − 1 RFS | $^a$% + 1 RFS | $^b$Killer phenotype |
|---|---|---|---|
| 1906 (mak8-1) | 5.18 ± 0.12% | 4.12% ± 0.16% | − |
| 980-10C + pRPL3 | 1.93 ± 0.18% | 5.34% ± 0.18% | + |
| 980-10C + pmak8-1 | 4.85 ± 0.12% | 5.47% ± 0.11% | − |

Assays of programmed −1 ribosomal frameshifting and the killer phenotype in yeast cells harboring the wild-type RPL3 gene or the mak8-1 allele. $^a$ % −1 ribosomal frameshifting was calculated by multiplying the ratio of p−1/p0 Beta-galactosidase activities by 100%. Absolute error is shown. $^b$Killer phenotype was determined as described in Materials and Methods.

EXAMPLE 3

Cloning of Tobacco L3 Genes

Applicants have conducted experiments in tobacco by introducing double gene constructs: wild-type L3 and wild-type PAP; Mak8-11 and wild-type PAP, and L3delta (encoding the 100 N-terminal amino acids of L3) and wild-type PAP. Expression of each coding sequence is driven by a separate CaMV 35S promoter. The transgenic plants show no phytotoxicity due to expression of high levels of wild-type PAP. The lack of phytotoxicity is particularly apparent when the plants are compared to other transgenic tobacco plants expressing wild-type PAP but not L3.

The L3 genes of tobacco (*Nicotiana tabacum* cv Samsun) have not been previously identified or characterized. We have isolated two full-length cDNA clones encoding two distinct L3 genes by screening a cDNA library constructed from tobacco leaves. The library was created in a phagemid vector using the ZAP Expression System by Stratagene. Screening of the cDNA library was followed according to the manufacturer's protocol.

The tobacco L3 genes were cloned by screening the lambda Zap library with the full-length cDNA of yeast L3 (RPL3 gene). Even though yeast L3 is only 68% homologous to *Arabidopsis* L3, sufficient sequence similarity exists to use the yeast L3 to probe the tobacco library. This probe was incubated with the phagemid DNA transferred to nitro-cellulose filters to allow hybridization. Positive matches were visualized by autoradiography and re-screened to confirm the hybridization. Positive pBK-CMV phagemid vectors were excised from the ZAP Express vector and transferred to XLOLR host cells (Stratagene), which contain a stable kanamycin selection gene.

The pBK-CMV phagemid DNA was purified from these XLOLR cells and the tobacco gene insert was released by digestion with the EcoRI and XhoI restriction enzymes. The resulting insert was 1.4 kb, comparable in size to the *Arabidopsis* L3 genes. The insert was characterized by DNA sequence analysis. Sequencing resulted in the identification of two distinct and complete cDNAs of tobacco L3 genes (8d and 10d). Unlike yeast, which has a single L3 gene, both *Arabidopsis* and rice contain two L3 genes. A BLAST database sequence search showed greatest similarity between the L3 genes of tobacco and *Arabidopsis*. The L3 genes of tobacco are 80% identical in nucleotide sequence. GCG analysis indicated that both L3 genes contain a complete open reading frame that translates a single protein of 389 amino acids (data not shown). This analysis was confirmed by in vitro transcription and translation of the two cDNAs in the TNT Coupled Reticulocyte Lysate System by Promega. The translation of either L3 genes produced a protein of approximately 44 kDa which was similar in molecular weight to yeast L3 at 43.5 kDa and the two *Arabidopsis* L3s, both at 44 kDa.

Construction of Plant Expression Vectors: NT286 (Tobacco L3-8d, Sense) and NT292 (Tobacco L3-8d, Antisense), NT243 (Yeast L3+PAP), NT244 (Yeast mak8+PAP)

Tobacco L3 gene 8d was cloned into the plant expression vector pEL103 downstream of the CaMV 35S promoter in sense orientation to generate NT286 and in antisense orientation to generate NT292.

The yeast L3 gene was cloned in sense orientation into the plant expression vector containing PAP to generate NT243 and mak8 was cloned in sense orientation into the plant expression vector containing PAP, to generate NT244. Expression of both L3 and mak8 genes was driven by the CaMV 35S promoter.

One of the two point mutations found in the yeast mak8 gene (P257S) was engineered into the tobacco L3 gene 8d in the vector NT315.

Transformation of tobacco plants with NT286, NT292, NT243, and NT244: NT286, 292, 243, and 244 were transformed into tobacco, Nicotiana tabacum cv Samsun N and n via Agrobacterium-mediated transformation. ELISA assays were performed on the regenerants to select NPTII-positive transgenic plants using an assay kit manufactured by Agdia.

Analysis of Transgenic Tobacco Plants (N. tabacum cv Samsun N), Containing NT243 (L3+PAP)

Out of 12 plants regenerated (N. tabacum cv Samsun N), ten were found to be NPTII-positive. These plants were numbered as NT243-2, 4, 5, 6, 7, 8, 9, 10, 11 and 12. PCR results demonstrated that both PAP and L3 genes can be detected in NT243-2, 6, 7, 8, 9, 10, 11 and 12. Immunoblot analysis revealed that PAP was expressed at various levels in these transgenic plants, with NT243-7 and NT243-9 as the highest, followed by NT243-6 and NT243-8. These results were strikingly different from the results reported in Lodge, et al., (1993). We observed a significant decrease in transformation frequencies with wild type PAP and generated only two transgenic lines with very low levels of expression. In contrast, we were able to generate 10 different transgenic lines when PAP was introduced together with yeast L3. Although the highest expressors NT243-7 and NT243-9 showed lesions on their leaves, the majority of these lines had normal phenotype. The observation that the other eight transgenic lines were free of mosaic symptoms suggests a possible interaction between wild type PAP and yeast L3, which can reduce or eliminate the cytotoxicity of PAP.

To determine whether transgenic tobacco plants containing NT243 were resistant to virus infection, 5 µg/ml tobacco mosaic virus (TMV) was inoculated onto two leaves (upper and lower) of NT243-2, 4, 6, and 8 lines. As shown in Table 3, these transgenic plants are highly resistant to TMV infection in terms of the local lesion numbers compared to wild type tobacco plants. These results suggest that the interaction between these two genes resulted in normal-looking plants and rendered the plants highly resistant to TMV infection.

TABLE 3

Susceptibility of transgenic tobacco plants to infection by 5 µg/ml TMV

| Line | Lesion # on lower leaf | Lesion # on upper leaf |
| --- | --- | --- |
| WT | 31 | 18 |
| NT243-2 | 0 | 0 |
| NT243-4 | 0 | 0 |
| NT243-6 | 0 | 2 |
| NT243-8 | 4 | 1 |
| NT244-1 | 20 | 8 |
| NT244-2 | 15 | 3 |
| NT286-5 | 9 | 8 |
| NT286-6 | 8 | 6 |
| NT292-2 | 29 | 7 |
| NT292-3 | 7 | 5 |

Analysis of Transgenic Tobacco Plants (N. tabacum cv Samsun N) Containing NT244 (mak8+PAP)T Three different transgenic tobacco plants (N. tabacum cv Samsun N) were generated. All three plants were phenotypically normal and indistinguishable from wild type tobacco plants. PCR analysis showed that both PAP and mak8 genes were present in these transgenic lines. Plants from lines NT244-1 and 2 showed lower numbers of local lesions, compared to the wild type plants (Table 3), indicating that they were resistant to TMV. However, the level of resistance was lower compared to NT243 (L3+PAP) plants.

Analysis of Transgenic Tobacco Plants (N. tabacum cv Samsun n) Containing NT243 and NT244

Eight different transgenic tobacco plants (N. tabacum cv Samsun n) were regenerated and confirmed to be transgenic by ELISA analysis for NT243. Similarly, eight different transgenic tobacco plants (N. tabacum cv Samsun n) were regenerated and confirmed to be transgenic by ELISA analysis for NT244. These plants were phenotypically indistinguishable from wild type tobacco plants, except NT243-2, which was slightly mosaic. Surprisingly however, PAP was expressed at relatively high levels in every plant. Yeast L3 expression was also detected in transgenic lines NT243-1, 2, 4, and 6.

Analysis of Transgenic Tobacco Plants Containing NT286 (Tobacco L3-8d, Sense) and NT292 (Tobacco L3-8d, Antisense)

Several transgenic tobacco plants were generated with NT286, containing the tobacco 8d gene in sense orientation and with NT292, containing the tobacco 8d gene in antisense orientation, as determined by ELISA. Two different transgenic lines NT286-5 and 6, containing the tobacco L3 gene in sense orientation and one transgenic line NT292-3, containing the tobacco L3 gene in antisense orientation showed resistance to TMV (Table 3).

Isolation of New L3 Mutants

The purpose of these experiments has been to identify new variants (alleles) of the yeast gene encoding ribosomal protein L3 (RPL3) that mimic the mak8-1 allele. The mak8-1 allele is incapable of maintaining an endogenous yeast virus called M1, and it is also resistant to pokeweed antiviral protein (PAP). Certain genetic conditions had to be established to allow for the identification of new rpl3 mutants. First, we had to accumulate a collection of mutant versions of the RPL3 gene. To do this, a plasmid-based clone harboring the wild-type RPL3 gene was passaged through E. coli XL-1 Red cells (commercially available from Stratagene Inc., La Jolla Calif.). The genetic makeup of these cells allows for the accumulation of multiple mutations in DNA sequences. The mixed population of plasmids harvested from the E. coli XL-1 Red cells constituted the collection or "library" of mutant rpl3 genes. Second, since the RPL3 gene is essential for life, we had to set up genetic conditions that would enable us to switch the mutant rpl3 genes for the wild-type RPL3 genes in cells. To do this, we constructed an RPL3 gene knockout yeast strain (rpl3-delta). Here, the RPL3 gene was deleted from the yeast chromosome, and a plasmid borne copy of RPL3 provides the gene product. The genetics were set up so that we could start with the rpl3-delta strain harboring the wild-type RPL3 gene on a plasmid, introduce another plasmid harboring mutant rpl3 (from the library), and then force the cells to lose the wild-type RPL3 copy. This was done by putting the wild-type gene on a URA3 plasmid, the library on a TRP1 plasmid, and selecting for growth on medium containing 5-flourootic acid, which serves as a URA3 poison. Cells that had lost the wild-type gene were then assayed for their ability to maintain the M1 virus by means of the standard yeast killer virus assay. To date, over 40 mutants have been identified. The DNA sequence of five of these has been determined. Interestingly, they are all identical: they harbor a single mutation at nucleotide residue 845 in the RPL3 gene that switches a cytosine for a thymidine base. This results in a change at amino acid residue 282, changing the wild-type isoleucine to a threonine. Interestingly, this mutation is close by the original mak8-1 mutations at amino acid residues 255 and 257.

The present invention has applicability in the field of agricultural biotechnology, and more particularly to the production of seed that produces transgenic plants exhibiting increased resistance to viruses and/or fungi that infect plants and tend to decrease yield. The trans-nucleic acid that imparts these properties to the plants is substantially non-toxic.

The present invention also has medical applications, particularly for conditions amenable to treatment with single-chain RIPs, particularly PAP, that bind endogenous L3 proteins but which exhibit a toxic effect on non-diseased cells.

The present invention further has industrial applications in the production of recombinant RIPs for pharmaceutical and therapeutic uses.

All patent and non-patent publications cited in this specification are herein incorporated by reference to the same extent as if each individual publication or patent application were specifically and individually indicated to be incorporated by reference.

The invention claimed is:

1. A transgenic plant containing an exogenous nucleic acid encoding a wild-type ribosomal L3 protein or a mutant ribosomal L3 protein which is rpl3-I282T designated as SEQ ID NO:12 or Mak 8 (W255C, p257S) designated as SEQ ID NO:10.

2. The transgenic plant of claim 1 wherein said nucleic acid is heterologous to said plant.

3. The transgenic plant of claim 1 wherein the L3 protein encoded by said nucleic acid is a wild-type ribosomal L3 protein.

4. The transgenic plant of claim 1 wherein said mutant ribosomal L3 protein is rpl3-I282T designated as SEQ ID NO:12.

5. The transgenic plant of claim 1 wherein said mutant ribosomal L3 protein is Mak8 (W255C, P257S) designated as SEQ ID NO:10.

6. The transgenic plant of claim 1 wherein said nucleic acid is a first exogenous nucleic acid and wherein said plant further comprises a second exogenous nucleic acid encoding a single chain ribosome inhibitory protein (RIP) that binds an endogenous ribosomal L3 protein.

7. The transgenic plant of claim 6 wherein the RIP encoded by said second nucleic acid is pokeweed antiviral protein (PAP), PAP-v or PAP II.

8. The transgenic plant of claim 1 that is a monocot plant.

9. The transgenic plant of claim 1 that is a dicot plant.

10. The transgenic plant of claim 1 that is a cereal crop plant.

11. A plant cell transformed with a nucleic acid encoding a wild-type ribosomal L3 protein or a mutant ribosomal L3 protein which is rpl3-I282T designated as SEQ ID NO:12 or Mak 8 (W255C, p257S) designated as SEQ ID NO:10.

12. A plant protoplast transformed with a nucleic acid encoding a wild-type ribosomal L3 protein or a mutant ribosomal L3 protein which is 3-I282T designated as SEQ ID NO:12 or Mak 8 (W255C, p257S) designated as SEQ ID NO:10.

13. Seed derived from the transgenic plant of claim 1, wherein the seed contains said exogenous nucleic acid.

14. A method of increasing resistance to viruses in a plant, comprising introducing an exogenous nucleic acid encoding a wild-type ribosomal L3 protein or a mutant ribosomal L3 protein which is rpl3-I282T designated as SEQ ID NO:12 or Mak 8 (W255C, p257S) designated as SEQ ID NO:10 into the plant whereby said exogenous nucleic acid is expressed, wherein expression of said nucleic acid in said plant results in increased resistance to viruses relative to a wild-type plant.

15. A method of reducing toxicity of a single chain ribosome inhibitory protein (RIP) contained in a plant, comprising introducing a first and a second exogenous nucleic acid into the plant thereby preparing a first transgenic plant, wherein the first exogenous nucleic acid encodes a wild-type ribosomal L3 protein or a mutant ribosomal L3 protein, which is rpl3-I282T designated as SEQ ID NO:12 or Mak 8 (W255C, p257S) designated as SEQ ID NO:10, and the second exogenous nucleic acid encodes a single chain ribosome inhibitory protein (RIP) that binds an endogenous L3 protein, whereby said first and second nucleic acids are expressed in said first transgenic plant, wherein expression of said first nucleic acid in said transgenic plant results in reduced toxicity to the RIP produced by expression of said second nucleic acid relative to a second transgenic plant expressing said second exogenous nucleic acid but not said first exogenous nucleic acid.

16. A method of preparing a plant having increased resistance to viruses and, comprising introducing an exogenous nucleic acid encoding a wild-type ribosomal L3 protein or mutant ribosomal L3 protein which is rpl3-I282T designated as SEQ ID NO:12 or Mak 8 (W255C, p257S) designated as SEQ ID NO:10 into a plant cell or protoplast to produce a transformed plant cell or protoplast, and regenerating a whole, transgenic plant from said transformed cell or protoplast, whereby said exogenous nucleic acid is expressed in said transgenic plant, wherein expression of said exogenous nucleic acid in said plant results in increased resistance to viruses relative to a wild-type plant.

17. A method of reducing toxicity to single chain ribosome inhibitory proteins (RIPs) in a plant, comprising introducing a first and a second exogenous nucleic acids into a plant cell or protoplast to produce a transformed plant cell or protoplast, wherein the first exogenous nucleic acid encodes a wild-type ribosomal L3 protein, and the second exogenous nucleic acid encodes a single chain ribosome inhibitory protein (RIP) that binds an endogenous L3 protein, and regenerating a first transgenic plant from said transformed cell or protoplast, whereby said first and second nucleic acids are expressed in said first transgenic plant, wherein expression of said first nucleic acid in said first transgenic plant results in reduced toxicity to the RIP produced by expression of said second nucleic acid relative to a second transgenic plant expressing said second exogenous nucleic acid but not said first exogenous nucleic acid.

18. An isolated nucleic acid encoding a mutant ribosomal L3 protein, which is rpl3-I282T designated as SEQ ID NO:12 or Mak 8 (W255C, p257S) designated as SEQ ID NO:10.

19. A cell, which is selected from the group consisting of plant, bacterium and yeast, transformed with the nucleic acid of claim 18.

20. The cell of claim 19 which is a bacterium or a yeast cell.

21. The cell of claim 19 which is the bacterium *E. coli.*

22. The cell of claim 19, which is a plant cell.

* * * * *

UNITED STATES PATENT AND TRADEMARK OFFICE
CERTIFICATE OF CORRECTION

| | | |
|---|---|---|
| PATENT NO. | : 7,235,715 B2 | Page 1 of 1 |
| APPLICATION NO. | : 10/636386 | |
| DATED | : June 26, 2007 | |
| INVENTOR(S) | : Nilgun E. Tumer, Jonathan D. Dinman and Katalin A. Hudak | |

It is certified that error appears in the above-identified patent and that said Letters Patent is hereby corrected as shown below:

Column 92, line 31 reads "3-I282T" should read --rp13-I282T--.
Column 92, line 63 reads "viruses and comprising" should read --viruses comprising--.

Signed and Sealed this

Twenty-third Day of September, 2008

JON W. DUDAS
*Director of the United States Patent and Trademark Office*

SEQUENCE LISTING

<160> NUMBER OF SEQ ID NOS: 14

<210> SEQ ID NO 1
<211> LENGTH: 1164
<212> TYPE: DNA
<213> ORGANISM: Saccharomyces cerevisiae
<220> FEATURE:
<221> NAME/KEY: CDS
<222> LOCATION: (1)..(1161)

<400> SEQUENCE: 1

```
atg tct cac aga aag tac gaa gca cca cgt cac ggt cat tta ggt ttc      48
Met Ser His Arg Lys Tyr Glu Ala Pro Arg His Gly His Leu Gly Phe
 1               5                  10                  15 ttg cca aga aag aga gct gcc tcc atc aga gct aga gtt aag gct ttt      96
Leu Pro Arg Lys Arg Ala Ala Ser Ile Arg Ala Arg Val Lys Ala Phe
             20                  25                  30 cca aag gat gac aga tcc aag cca gtt gct cta act tcc ttc ttg ggt     144
Pro Lys Asp Asp Arg Ser Lys Pro Val Ala Leu Thr Ser Phe Leu Gly
         35                  40                  45 tac aag gct ggt atg acc acc att gtc aga gat ttg gac aga cca ggt     192
Tyr Lys Ala Gly Met Thr Thr Ile Val Arg Asp Leu Asp Arg Pro Gly
     50                  55                  60 tct aag ttc cac aag cgt gaa gtt gtc gaa gct gtc acc gtt gtt gac     240
Ser Lys Phe His Lys Arg Glu Val Val Glu Ala Val Thr Val Val Asp
 65                  70                  75                  80 act cca cca gtt gtc gtt gtt ggt gtt gtc ggt tac gtc gaa acc cca     288
Thr Pro Pro Val Val Val Val Gly Val Val Gly Tyr Val Glu Thr Pro
                 85                  90                  95 aga ggt ttg aga tct ttg acc acc gtc tgg gct gaa cat ttg tct gac     336
Arg Gly Leu Arg Ser Leu Thr Thr Val Trp Ala Glu His Leu Ser Asp
            100                 105                 110 gaa gtc aag aga aga ttc tac aag aac tgg tac aag tct aag aag aag     384
Glu Val Lys Arg Arg Phe Tyr Lys Asn Trp Tyr Lys Ser Lys Lys Lys
        115                 120                 125 gct ttc acc aaa tac tct gcc aag tac gct caa gat ggt gct ggt att     432
Ala Phe Thr Lys Tyr Ser Ala Lys Tyr Ala Gln Asp Gly Ala Gly Ile
    130                 135                 140 gaa aga gaa ttg gct aga atc aag aag tac gct tcc gtc gtc aga gtt     480
Glu Arg Glu Leu Ala Arg Ile Lys Lys Tyr Ala Ser Val Val Arg Val
145                 150                 155                 160
```

```
ttg gtc cac act caa atc aga aag act cca ttg gct caa aag aag gct       528
Leu Val His Thr Gln Ile Arg Lys Thr Pro Leu Ala Gln Lys Lys Ala
            165                 170                 175 cat ttg gct gaa atc caa ttg aac ggt ggt tcc atc tct gaa aag gtt       576
His Leu Ala Glu Ile Gln Leu Asn Gly Gly Ser Ile Ser Glu Lys Val
        180                 185                 190 gac tgg gct cgt gaa cat ttc gaa aag act gtt gct gtc gac agc gtt       624
Asp Trp Ala Arg Glu His Phe Glu Lys Thr Val Ala Val Asp Ser Val
    195                 200                 205 ttt gaa caa aac gaa atg att gac gct att gct gtc acc aag ggt cac       672
Phe Glu Gln Asn Glu Met Ile Asp Ala Ile Ala Val Thr Lys Gly His
210                 215                 220 ggt ttc gaa ggt gtt acc cac aga tgg ggt act aag aaa ttg cca aga       720
Gly Phe Glu Gly Val Thr His Arg Trp Gly Thr Lys Lys Leu Pro Arg
225                 230                 235                 240 aag act cac aga ggt cta aga aag gtt gct tgt att ggt gct tgg cat       768
Lys Thr His Arg Gly Leu Arg Lys Val Ala Cys Ile Gly Ala Trp His
                245                 250                 255 cca gcc cac gtt atg tgg agt gtt gcc aga gct ggt caa aga ggt tac       816
Pro Ala His Val Met Trp Ser Val Ala Arg Ala Gly Gln Arg Gly Tyr
            260                 265                 270 cat tcc aga acc tcc att aac cac aag att tac aga gtc ggt aag ggt       864
His Ser Arg Thr Ser Ile Asn His Lys Ile Tyr Arg Val Gly Lys Gly
        275                 280                 285 gat gat gaa gct aac ggt gct acc agc ttc gac aga acc aag aag act       912
Asp Asp Glu Ala Asn Gly Ala Thr Ser Phe Asp Arg Thr Lys Lys Thr
    290                 295                 300 att acc cca atg ggt ggt ttc gtc cac tac ggt gaa att aag aac gac       960
Ile Thr Pro Met Gly Gly Phe Val His Tyr Gly Glu Ile Lys Asn Asp
305                 310                 315                 320 ttc atc atg gtt aaa ggt tgt atc cca ggt aac aga aag aga att gtt      1008
Phe Ile Met Val Lys Gly Cys Ile Pro Gly Asn Arg Lys Arg Ile Val
                325                 330                 335 act ttg aga aag tct ttg tac acc aac act tct aga aag gct ttg gaa      1056
Thr Leu Arg Lys Ser Leu Tyr Thr Asn Thr Ser Arg Lys Ala Leu Glu
            340                 345                 350 gaa gtc agc ttg aag tgg att gac act gct tct aag ttc ggt aag ggt      1104
Glu Val Ser Leu Lys Trp Ile Asp Thr Ala Ser Lys Phe Gly Lys Gly
        355                 360                 365 aga ttc caa acc cca gct gaa aag cat gct ttc atg ggt act ttg aag      1152
Arg Phe Gln Thr Pro Ala Glu Lys His Ala Phe Met Gly Thr Leu Lys
    370                 375                 380 aag gac ttg taa                                                      1164
Lys Asp Leu
385

<210> SEQ ID NO 2
<211> LENGTH: 387
<212> TYPE: PRT
<213> ORGANISM: Saccharomyces cerevisiae

<400> SEQUENCE: 2

Met Ser His Arg Lys Tyr Glu Ala Pro Arg His Gly His Leu Gly Phe
 1               5                  10                  15

Leu Pro Arg Lys Arg Ala Ala Ser Ile Arg Ala Arg Val Lys Ala Phe
            20                  25                  30

Pro Lys Asp Asp Arg Ser Lys Pro Val Ala Leu Thr Ser Phe Leu Gly
        35                  40                  45

Tyr Lys Ala Gly Met Thr Thr Ile Val Arg Asp Leu Asp Arg Pro Gly
```

```
                50                      55                      60
Ser Lys Phe His Lys Arg Glu Val Val Glu Ala Val Thr Val Val Asp
 65                      70                      75                      80

Thr Pro Pro Val Val Val Gly Val Gly Tyr Val Glu Thr Pro
                     85                      90                      95

Arg Gly Leu Arg Ser Leu Thr Thr Val Trp Ala Glu His Leu Ser Asp
                    100                     105                     110

Glu Val Lys Arg Arg Phe Tyr Lys Asn Trp Tyr Lys Ser Lys Lys
                115                     120                     125

Ala Phe Thr Lys Tyr Ser Ala Lys Tyr Ala Gln Asp Gly Ala Gly Ile
            130                     135                     140

Glu Arg Glu Leu Ala Arg Ile Lys Lys Tyr Ala Ser Val Val Arg Val
145                     150                     155                     160

Leu Val His Thr Gln Ile Arg Lys Thr Pro Leu Ala Gln Lys Lys Ala
                    165                     170                     175

His Leu Ala Glu Ile Gln Leu Asn Gly Gly Ser Ile Ser Glu Lys Val
                180                     185                     190

Asp Trp Ala Arg Glu His Phe Glu Lys Thr Val Ala Val Asp Ser Val
            195                     200                     205

Phe Glu Gln Asn Glu Met Ile Asp Ala Ile Ala Val Thr Lys Gly His
    210                     215                     220

Gly Phe Glu Gly Val Thr His Arg Trp Gly Thr Lys Lys Leu Pro Arg
225                     230                     235                     240

Lys Thr His Arg Gly Leu Arg Lys Val Ala Cys Ile Gly Ala Trp His
                    245                     250                     255

Pro Ala His Val Met Trp Ser Val Ala Arg Ala Gly Gln Arg Gly Tyr
                260                     265                     270

His Ser Arg Thr Ser Ile Asn His Lys Ile Tyr Arg Val Gly Lys Gly
            275                     280                     285

Asp Asp Glu Ala Asn Gly Ala Thr Ser Phe Asp Arg Thr Lys Lys Thr
290                     295                     300

Ile Thr Pro Met Gly Gly Phe Val His Tyr Gly Glu Ile Lys Asn Asp
305                     310                     315                     320

Phe Ile Met Val Lys Gly Cys Ile Pro Gly Asn Arg Lys Arg Ile Val
                    325                     330                     335

Thr Leu Arg Lys Ser Leu Tyr Thr Asn Thr Ser Arg Lys Ala Leu Glu
                340                     345                     350

Glu Val Ser Leu Lys Trp Ile Asp Thr Ala Ser Lys Phe Gly Lys Gly
            355                     360                     365

Arg Phe Gln Thr Pro Ala Glu Lys His Ala Phe Met Gly Thr Leu Lys
370                     375                     380

Lys Asp Leu
385

<210> SEQ ID NO 3
<211> LENGTH: 1170
<212> TYPE: DNA
<213> ORGANISM: Nicotiana tabacum
<220> FEATURE:
<221> NAME/KEY: CDS
<222> LOCATION: (1)..(1167)

<400> SEQUENCE: 3 atg tct cac agg aag ttt gag cat cca aga cac ggt tct ttg gga ttt      48
Met Ser His Arg Lys Phe Glu His Pro Arg His Gly Ser Leu Gly Phe
  1               5                  10                  15
```

| | | |
|---|---|---|
| ctg ccc agg aag cgt gct gcc aga cac agg gga aag gtg aag gca ttc<br>Leu Pro Arg Lys Arg Ala Ala Arg His Arg Gly Lys Val Lys Ala Phe<br>             20                                  25                              30 | | 96 |
| cca aaa gat gat cca aac aag ccc tgc aag cta act gcc ttc ttg ggc<br>Pro Lys Asp Asp Pro Asn Lys Pro Cys Lys Leu Thr Ala Phe Leu Gly<br>35                            40                               45 | | 144 |
| tac aaa gct ggc atg act cac att gtc aga gat gtt gaa aaa cct gga<br>Tyr Lys Ala Gly Met Thr His Ile Val Arg Asp Val Glu Lys Pro Gly<br>     50                           55                            60 | | 192 |
| tca aaa ctc cac aag aaa gag aca tgt gaa gct gtc acc atc att gaa<br>Ser Lys Leu His Lys Lys Glu Thr Cys Glu Ala Val Thr Ile Ile Glu<br>65                           70                            75                        80 | | 240 |
| aca cct cca atg gtg att gtt ggt gtt gtt ggg tat gtg aag aca cct<br>Thr Pro Pro Met Val Ile Val Gly Val Val Gly Tyr Val Lys Thr Pro<br>                     85                            90                            95 | | 288 |
| cgt ggt ctt cgt tgc ctg aac act gtc tgg gct caa cat ctc agt gaa<br>Arg Gly Leu Arg Cys Leu Asn Thr Val Trp Ala Gln His Leu Ser Glu<br>               100                          105                         110 | | 336 |
| gag ctt aag agg agg ttc tac aag aac tgg tgc aag tcc aag aag aag<br>Glu Leu Lys Arg Arg Phe Tyr Lys Asn Trp Cys Lys Ser Lys Lys Lys<br>115                          120                           125 | | 384 |
| gcc ttc ttg aaa tac tcc aag aaa tat gaa tct gat gaa ggg aaa aag<br>Ala Phe Leu Lys Tyr Ser Lys Lys Tyr Glu Ser Asp Glu Gly Lys Lys<br>     130                           135                          140 | | 432 |
| gac atc cag aca cag ctg gag aaa ttg aag aag tat gca tgc gtc atc<br>Asp Ile Gln Thr Gln Leu Glu Lys Leu Lys Lys Tyr Ala Cys Val Ile<br>145                         150                        155                        160 | | 480 |
| cgt gtt ttg gct cac act cag ata agg aag atg aag ggt ctg aaa cag<br>Arg Val Leu Ala His Thr Gln Ile Arg Lys Met Lys Gly Leu Lys Gln<br>               165                          170                         175 | | 528 |
| aag aaa gcc cat ttg atg gag ata cag gtg aat gga ggg aca att gct<br>Lys Lys Ala His Leu Met Glu Ile Gln Val Asn Gly Gly Thr Ile Ala<br>     180                           185                          190 | | 576 |
| cag aag gtt gac ttt gca tat ggt ttc ttc gag aag cag gtt cca gtt<br>Gln Lys Val Asp Phe Ala Tyr Gly Phe Phe Glu Lys Gln Val Pro Val<br>               195                          200                         205 | | 624 |
| gat gct gtt ttt cag aag gat gag atg att gac atc att ggt gtc acc<br>Asp Ala Val Phe Gln Lys Asp Glu Met Ile Asp Ile Ile Gly Val Thr<br>210                         215                        220 | | 672 |
| aag ggt aag ggt tat gaa ggt gtt gta act cgt tgg ggt gtg aca cgt<br>Lys Gly Lys Gly Tyr Glu Gly Val Val Thr Arg Trp Gly Val Thr Arg<br>225                         230                        235                        240 | | 720 |
| ctt cct cgc aaa acc cac agg ggt ctg cgt aag gtt gct tgt att gga<br>Leu Pro Arg Lys Thr His Arg Gly Leu Arg Lys Val Ala Cys Ile Gly<br>               245                          250                         255 | | 768 |
| gcc tgg cac cct gct aga gtt tcc tac aca gtt gcc cgt gct ggt caa<br>Ala Trp His Pro Ala Arg Val Ser Tyr Thr Val Ala Arg Ala Gly Gln<br>     260                           265                          270 | | 816 |
| aat gga tac cat cac cgt acc gag atg aac aag aag gtt tac aaa cta<br>Asn Gly Tyr His His Arg Thr Glu Met Asn Lys Lys Val Tyr Lys Leu<br>               275                          280                         285 | | 864 |
| ggg aag gct ggc caa gag tcc cat gct gct gta act gat ttt gac agg<br>Gly Lys Ala Gly Gln Glu Ser His Ala Ala Val Thr Asp Phe Asp Arg<br>290                         295                        300 | | 912 |
| acc gag aaa gac att act ccc atg ggt gga ttt ccc cat tat ggt gtg<br>Thr Glu Lys Asp Ile Thr Pro Met Gly Gly Phe Pro His Tyr Gly Val<br>305                         310                        315                        320 | | 960 |
| gtg aag gat gat tac ctg ttg atc aag gga tgc tgt gtt ggt cct aag<br>Val Lys Asp Asp Tyr Leu Leu Ile Lys Gly Cys Cys Val Gly Pro Lys | | 1008 |

-continued

```
                     325                 330                 335
aag agg gtt gta acc ctt cgt cag tcc ctg ctc aac cag acc tct cgt      1056
Lys Arg Val Val Thr Leu Arg Gln Ser Leu Leu Asn Gln Thr Ser Arg
            340                 345                 350 gtc gct ctt gag gag att aag ctg aag ttc atc gat aca tcc tca aag      1104
Val Ala Leu Glu Glu Ile Lys Leu Lys Phe Ile Asp Thr Ser Ser Lys
        355                 360                 365 ttt gga cat ggt cgc ttc cag acc act caa gag aag cag aaa ttc tat      1152
Phe Gly His Gly Arg Phe Gln Thr Thr Gln Glu Lys Gln Lys Phe Tyr
    370                 375                 380 ggc cgg ttg aag ggt taa                                               1170
Gly Arg Leu Lys Gly
385
```

<210> SEQ ID NO 4
<211> LENGTH: 389
<212> TYPE: PRT
<213> ORGANISM: Nicotiana tabacum

<400> SEQUENCE: 4

```
Met Ser His Arg Lys Phe Glu His Pro Arg His Gly Ser Leu Gly Phe
 1               5                  10                  15

Leu Pro Arg Lys Arg Ala Ala Arg His Arg Gly Lys Val Lys Ala Phe
            20                  25                  30

Pro Lys Asp Asp Pro Asn Lys Pro Cys Lys Leu Thr Ala Phe Leu Gly
        35                  40                  45

Tyr Lys Ala Gly Met Thr His Ile Val Arg Asp Val Glu Lys Pro Gly
    50                  55                  60

Ser Lys Leu His Lys Lys Glu Thr Cys Glu Ala Val Thr Ile Ile Glu
65                  70                  75                  80

Thr Pro Pro Met Val Ile Val Gly Val Gly Tyr Val Lys Thr Pro
                85                  90                  95

Arg Gly Leu Arg Cys Leu Asn Thr Val Trp Ala Gln His Leu Ser Glu
            100                 105                 110

Glu Leu Lys Arg Arg Phe Tyr Lys Asn Trp Cys Lys Ser Lys Lys Lys
        115                 120                 125

Ala Phe Leu Lys Tyr Ser Lys Lys Tyr Glu Ser Asp Glu Gly Lys Lys
    130                 135                 140

Asp Ile Gln Thr Gln Leu Glu Lys Leu Lys Lys Tyr Ala Cys Val Ile
145                 150                 155                 160

Arg Val Leu Ala His Thr Gln Ile Arg Lys Met Lys Gly Leu Lys Gln
                165                 170                 175

Lys Lys Ala His Leu Met Glu Ile Gln Val Asn Gly Gly Thr Ile Ala
            180                 185                 190

Gln Lys Val Asp Phe Ala Tyr Gly Phe Phe Glu Lys Gln Val Pro Val
        195                 200                 205

Asp Ala Val Phe Gln Lys Asp Glu Met Ile Asp Ile Gly Val Thr
    210                 215                 220

Lys Gly Lys Gly Tyr Glu Gly Val Val Thr Arg Trp Gly Val Thr Arg
225                 230                 235                 240

Leu Pro Arg Lys Thr His Arg Gly Leu Arg Lys Val Ala Cys Ile Gly
                245                 250                 255

Ala Trp His Pro Ala Arg Val Ser Tyr Thr Val Ala Arg Ala Gly Gln
            260                 265                 270

Asn Gly Tyr His His Arg Thr Glu Met Asn Lys Lys Val Tyr Lys Leu
        275                 280                 285
```

```
Gly Lys Ala Gly Gln Glu Ser His Ala Ala Val Thr Asp Phe Asp Arg
    290                 295                 300

Thr Glu Lys Asp Ile Thr Pro Met Gly Gly Phe Pro His Tyr Gly Val
305                 310                 315                 320

Val Lys Asp Asp Tyr Leu Leu Ile Lys Gly Cys Cys Val Gly Pro Lys
                325                 330                 335

Lys Arg Val Val Thr Leu Arg Gln Ser Leu Leu Asn Gln Thr Ser Arg
            340                 345                 350

Val Ala Leu Glu Glu Ile Lys Leu Lys Phe Ile Asp Thr Ser Ser Lys
        355                 360                 365

Phe Gly His Gly Arg Phe Gln Thr Thr Gln Glu Lys Gln Lys Phe Tyr
    370                 375                 380

Gly Arg Leu Lys Gly
385

<210> SEQ ID NO 5
<211> LENGTH: 1170
<212> TYPE: DNA
<213> ORGANISM: Nicotiana tabacum
<220> FEATURE:
<221> NAME/KEY: CDS
<222> LOCATION: (1)..(1167)

<400> SEQUENCE: 5
```

| | | | | | | | | | | | | | | | | |
|---|---|---|---|---|---|---|---|---|---|---|---|---|---|---|---|---|
| atg | tcg | cat | cgc | aag | ttt | gag | cac | cca | aga | cac | ggt | tct | ttg | gga | ttt | 48 |
| Met | Ser | His | Arg | Lys | Phe | Glu | His | Pro | Arg | His | Gly | Ser | Leu | Gly | Phe | |
| 1 | | | | 5 | | | | | 10 | | | | | 15 | | |
| ctt | cca | agg | aaa | aga | gca | gca | cga | cac | agg | ggc | aaa | gtg | aag | gct | ttt | 96 |
| Leu | Pro | Arg | Lys | Arg | Ala | Ala | Arg | His | Arg | Gly | Lys | Val | Lys | Ala | Phe | |
| | | | 20 | | | | | 25 | | | | | 30 | | | |
| ccc | aaa | gat | gat | aca | aca | aaa | cct | tgc | agg | ttg | aca | gct | ttc | ctt | ggc | 144 |
| Pro | Lys | Asp | Asp | Thr | Thr | Lys | Pro | Cys | Arg | Leu | Thr | Ala | Phe | Leu | Gly | |
| | | 35 | | | | | 40 | | | | | 45 | | | | |
| tac | aaa | gct | ggt | atg | act | cat | att | gtc | aga | gat | gtt | gaa | aaa | cca | ggg | 192 |
| Tyr | Lys | Ala | Gly | Met | Thr | His | Ile | Val | Arg | Asp | Val | Glu | Lys | Pro | Gly | |
| | 50 | | | | | 55 | | | | | 60 | | | | | |
| tca | aaa | ctc | cat | aag | aaa | gaa | aca | tgc | gaa | ctg | gtt | acc | ata | att | gaa | 240 |
| Ser | Lys | Leu | His | Lys | Lys | Glu | Thr | Cys | Glu | Leu | Val | Thr | Ile | Ile | Glu | |
| 65 | | | | | 70 | | | | | 75 | | | | | 80 | |
| acg | cct | cct | atg | att | gtt | gtt | ggg | gtt | gtt | ggc | tat | gtg | aaa | aca | cca | 288 |
| Thr | Pro | Pro | Met | Ile | Val | Val | Gly | Val | Val | Gly | Tyr | Val | Lys | Thr | Pro | |
| | | | | 85 | | | | | 90 | | | | | 95 | | |
| cgt | ggc | ctt | cgc | tgc | ctt | agc | acg | gtc | tgg | gct | caa | cat | ctt | agt | gaa | 336 |
| Arg | Gly | Leu | Arg | Cys | Leu | Ser | Thr | Val | Trp | Ala | Gln | His | Leu | Ser | Glu | |
| | | | 100 | | | | | 105 | | | | | 110 | | | |
| gag | att | aaa | agg | aga | ttc | tac | aag | aac | tgg | tgc | atg | tcc | aaa | aag | aag | 384 |
| Glu | Ile | Lys | Arg | Arg | Phe | Tyr | Lys | Asn | Trp | Cys | Met | Ser | Lys | Lys | Lys | |
| | | 115 | | | | | 120 | | | | | 125 | | | | |
| gcc | ttt | gca | aag | tac | tcg | aag | aag | tat | gaa | act | gat | gat | ggt | aag | aag | 432 |
| Ala | Phe | Ala | Lys | Tyr | Ser | Lys | Lys | Tyr | Glu | Thr | Asp | Asp | Gly | Lys | Lys | |
| | 130 | | | | | 135 | | | | | 140 | | | | | |
| gat | att | aat | gcg | caa | ttg | gag | aag | atg | aag | aag | tat | tgt | tgt | gtc | att | 480 |
| Asp | Ile | Asn | Ala | Gln | Leu | Glu | Lys | Met | Lys | Lys | Tyr | Cys | Cys | Val | Ile | |
| 145 | | | | | 150 | | | | | 155 | | | | | 160 | |
| cgt | gtt | ttg | gcc | cat | act | cag | att | aga | aaa | atg | aaa | ggt | ctc | aag | caa | 528 |
| Arg | Val | Leu | Ala | His | Thr | Gln | Ile | Arg | Lys | Met | Lys | Gly | Leu | Lys | Gln | |
| | | | | 165 | | | | | 170 | | | | | 175 | | |
| aag | aag | gca | cat | ctg | atg | gag | att | cag | gtt | aat | ggt | ggg | gat | gtt | tcc | 576 |
| Lys | Lys | Ala | His | Leu | Met | Glu | Ile | Gln | Val | Asn | Gly | Gly | Asp | Val | Ser | |

```
                    180                 185                 190
cag aag gtt gat tat gct tat ggc ttc ttt gag aag cag att cct gtt       624
Gln Lys Val Asp Tyr Ala Tyr Gly Phe Phe Glu Lys Gln Ile Pro Val
            195                 200                 205 gat gct att ttc caa aag gat gag atg atc gat att att ggt gtg acc       672
Asp Ala Ile Phe Gln Lys Asp Glu Met Ile Asp Ile Ile Gly Val Thr
        210                 215                 220 aaa ggt aag ggt tat gag ggt gtg gtg act cgt tgg ggt gta acc cgt       720
Lys Gly Lys Gly Tyr Glu Gly Val Val Thr Arg Trp Gly Val Thr Arg
225                 230                 235                 240 ctc cca cgt aag acc cat cgt ggt ctt aga aag gtg gct tgt att ggt       768
Leu Pro Arg Lys Thr His Arg Gly Leu Arg Lys Val Ala Cys Ile Gly
                245                 250                 255 gct tgg cat cca gca cgg gtg tca tac act gta gct agg gct ggg cag       816
Ala Trp His Pro Ala Arg Val Ser Tyr Thr Val Ala Arg Ala Gly Gln
            260                 265                 270 aat ggt tat cac cat cgc act gag ctg aac aag aaa gtc tac agg ctg       864
Asn Gly Tyr His His Arg Thr Glu Leu Asn Lys Lys Val Tyr Arg Leu
        275                 280                 285 ggc aag gct ggt cag gag tct cat tct gca ata act gag ttt gac agg       912
Gly Lys Ala Gly Gln Glu Ser His Ser Ala Ile Thr Glu Phe Asp Arg
    290                 295                 300 act gag aag gat atc acg cca atg ggt gga ttt cct cat tat ggt att       960
Thr Glu Lys Asp Ile Thr Pro Met Gly Gly Phe Pro His Tyr Gly Ile
305                 310                 315                 320 gtg aaa gaa gac ttt ctg ttg att aag ggc tgc tgt gtt gga cca aag      1008
Val Lys Glu Asp Phe Leu Leu Ile Lys Gly Cys Cys Val Gly Pro Lys
                325                 330                 335 aag cgt gtt gtg act ctg agg cag tct ctg ttg aat cag aca tct agg      1056
Lys Arg Val Val Thr Leu Arg Gln Ser Leu Leu Asn Gln Thr Ser Arg
            340                 345                 350 gtt gca ttg gag gag atc aag ctc aag ttc att gac aca tcc tcc aag      1104
Val Ala Leu Glu Glu Ile Lys Leu Lys Phe Ile Asp Thr Ser Ser Lys
        355                 360                 365 ttt ggc cat gga cgc ttc cag act aca cag gag aag gac aaa ttc tat      1152
Phe Gly His Gly Arg Phe Gln Thr Thr Gln Glu Lys Asp Lys Phe Tyr
    370                 375                 380 gga cgt ctt aaa gct tga                                              1170
Gly Arg Leu Lys Ala
385

<210> SEQ ID NO 6
<211> LENGTH: 389
<212> TYPE: PRT
<213> ORGANISM: Nicotiana tabacum

<400> SEQUENCE: 6

Met Ser His Arg Lys Phe Glu His Pro Arg His Gly Ser Leu Gly Phe
1               5                   10                  15

Leu Pro Arg Lys Arg Ala Ala Arg His Arg Gly Lys Val Lys Ala Phe
            20                  25                  30

Pro Lys Asp Asp Thr Thr Lys Pro Cys Arg Leu Thr Ala Phe Leu Gly
        35                  40                  45

Tyr Lys Ala Gly Met Thr His Ile Val Arg Asp Val Glu Lys Pro Gly
    50                  55                  60

Ser Lys Leu His Lys Lys Glu Thr Cys Glu Leu Val Thr Ile Ile Glu
65                  70                  75                  80

Thr Pro Pro Met Ile Val Val Gly Val Val Gly Tyr Val Lys Thr Pro
                85                  90                  95
```

```
Arg Gly Leu Arg Cys Leu Ser Thr Val Trp Ala Gln His Leu Ser Glu
            100                 105                 110

Glu Ile Lys Arg Arg Phe Tyr Lys Asn Trp Cys Met Ser Lys Lys
        115                 120                 125

Ala Phe Ala Lys Tyr Ser Lys Tyr Glu Thr Asp Asp Gly Lys Lys
130                 135                 140

Asp Ile Asn Ala Gln Leu Glu Lys Met Lys Tyr Cys Cys Val Ile
145                 150                 155                 160

Arg Val Leu Ala His Thr Gln Ile Arg Lys Met Lys Gly Leu Lys Gln
                165                 170                 175

Lys Lys Ala His Leu Met Glu Ile Gln Val Asn Gly Gly Asp Val Ser
                180                 185                 190

Gln Lys Val Asp Tyr Ala Tyr Gly Phe Phe Glu Lys Gln Ile Pro Val
            195                 200                 205

Asp Ala Ile Phe Gln Lys Asp Glu Met Ile Asp Ile Ile Gly Val Thr
210                 215                 220

Lys Gly Lys Gly Tyr Glu Gly Val Val Thr Arg Trp Gly Val Thr Arg
225                 230                 235                 240

Leu Pro Arg Lys Thr His Arg Gly Leu Arg Lys Val Ala Cys Ile Gly
                245                 250                 255

Ala Trp His Pro Ala Arg Val Ser Tyr Thr Val Ala Arg Ala Gly Gln
            260                 265                 270

Asn Gly Tyr His His Arg Thr Glu Leu Asn Lys Lys Val Tyr Arg Leu
        275                 280                 285

Gly Lys Ala Gly Gln Glu Ser His Ser Ala Ile Thr Glu Phe Asp Arg
290                 295                 300

Thr Glu Lys Asp Ile Thr Pro Met Gly Gly Phe Pro His Tyr Gly Ile
305                 310                 315                 320

Val Lys Glu Asp Phe Leu Leu Ile Lys Gly Cys Cys Val Gly Pro Lys
                325                 330                 335

Lys Arg Val Val Thr Leu Arg Gln Ser Leu Leu Asn Gln Thr Ser Arg
            340                 345                 350

Val Ala Leu Glu Glu Ile Lys Leu Lys Phe Ile Asp Thr Ser Ser Lys
        355                 360                 365

Phe Gly His Gly Arg Phe Gln Thr Thr Gln Glu Lys Asp Lys Phe Tyr
    370                 375                 380

Gly Arg Leu Lys Ala
385

<210> SEQ ID NO 7
<211> LENGTH: 1164
<212> TYPE: DNA
<213> ORGANISM: Saccharomyces cerevisiae
<220> FEATURE:
<221> NAME/KEY: CDS
<222> LOCATION: (1)..(1161)

<400> SEQUENCE: 7 atg tct cac aga aag tac gaa gca cca cgt cac ggt cat tta ggt ttc     48
Met Ser His Arg Lys Tyr Glu Ala Pro Arg His Gly His Leu Gly Phe
  1               5                  10                  15 ttg cca aga aag aga gct gcc tcc atc aga gct aga gtt aag gct ttt     96
Leu Pro Arg Lys Arg Ala Ala Ser Ile Arg Ala Arg Val Lys Ala Phe
             20                  25                  30 cca aag gat gac aga tcc aag cca gtt gct cta act tcc ttc ttg ggt    144
Pro Lys Asp Asp Arg Ser Lys Pro Val Ala Leu Thr Ser Phe Leu Gly
```

-continued

```
                35                  40                  45
tac aag gct ggt atg acc acc att gtc aga gat ttg gac aga cca ggt      192
Tyr Lys Ala Gly Met Thr Thr Ile Val Arg Asp Leu Asp Arg Pro Gly
     50                  55                  60 tct aag ttc cac aag cgt gaa gtt gtc gaa gct gtc acc gtt gtt gac      240
Ser Lys Phe His Lys Arg Glu Val Val Glu Ala Val Thr Val Val Asp
 65                  70                  75                  80 act cca cca gtt gtc gtt gtt ggt gtt gtc ggt tac gtc gaa acc cca      288
Thr Pro Pro Val Val Val Val Gly Val Val Gly Tyr Val Glu Thr Pro
                 85                  90                  95 aga ggt ttg aga tct ttg acc acc gtc tgg gct gaa cat ttg tct gac      336
Arg Gly Leu Arg Ser Leu Thr Thr Val Trp Ala Glu His Leu Ser Asp
            100                 105                 110 gaa gtc aag aga aga ttc tac aag aac tgg tac aag tct aag aag aag      384
Glu Val Lys Arg Arg Phe Tyr Lys Asn Trp Tyr Lys Ser Lys Lys Lys
        115                 120                 125 gct ttc acc aaa tac tct gcc aag tac gct caa gat ggt gct ggt att      432
Ala Phe Thr Lys Tyr Ser Ala Lys Tyr Ala Gln Asp Gly Ala Gly Ile
    130                 135                 140 gaa aga gaa ttg gct aga atc aag aag tac gct tcc gtc gtc aga gtt      480
Glu Arg Glu Leu Ala Arg Ile Lys Lys Tyr Ala Ser Val Val Arg Val
145                 150                 155                 160 ttg gtc cac act caa atc aga aag act cca ttg gct caa aag aag gct      528
Leu Val His Thr Gln Ile Arg Lys Thr Pro Leu Ala Gln Lys Lys Ala
                165                 170                 175 cat ttg gct gaa atc caa ttg aac ggt ggt tcc atc tct gaa aag gtt      576
His Leu Ala Glu Ile Gln Leu Asn Gly Gly Ser Ile Ser Glu Lys Val
            180                 185                 190 gac tgg gct cgt gaa cat ttc gaa aag act gtt gct gtc gac agc gtt      624
Asp Trp Ala Arg Glu His Phe Glu Lys Thr Val Ala Val Asp Ser Val
        195                 200                 205 ttt gaa caa aac gaa atg att gac gct att gct gtc acc aag ggt cac      672
Phe Glu Gln Asn Glu Met Ile Asp Ala Ile Ala Val Thr Lys Gly His
    210                 215                 220 ggt ttc gaa ggt gtt acc cac aga tgg ggt act aag aaa ttg cca aga      720
Gly Phe Glu Gly Val Thr His Arg Trp Gly Thr Lys Lys Leu Pro Arg
225                 230                 235                 240 aag act cac aga ggt cta aga aag gtt gct tgt att ggt gct tgc cat      768
Lys Thr His Arg Gly Leu Arg Lys Val Ala Cys Ile Gly Ala Cys His
                245                 250                 255 cca gcc cac gtt atg tgg agt gtt gcc aga gct ggt caa aga ggt tac      816
Pro Ala His Val Met Trp Ser Val Ala Arg Ala Gly Gln Arg Gly Tyr
            260                 265                 270 cat tcc aga acc tcc att aac cac aag att tac aga gtc ggt aag ggt      864
His Ser Arg Thr Ser Ile Asn His Lys Ile Tyr Arg Val Gly Lys Gly
        275                 280                 285 gat gat gaa gct aac ggt gct acc agc ttc gac aga acc aag aag act      912
Asp Asp Glu Ala Asn Gly Ala Thr Ser Phe Asp Arg Thr Lys Lys Thr
    290                 295                 300 att acc cca atg ggt ggt ttc gtc cac tac ggt gaa att aag aac gac      960
Ile Thr Pro Met Gly Gly Phe Val His Tyr Gly Glu Ile Lys Asn Asp
305                 310                 315                 320 ttc atc atg gtt aaa ggt tgt atc cca ggt aac aga aag aga att gtt     1008
Phe Ile Met Val Lys Gly Cys Ile Pro Gly Asn Arg Lys Arg Ile Val
                325                 330                 335 act ttg aga aag tct ttg tac acc aac act tct aga aag gct ttg gaa     1056
Thr Leu Arg Lys Ser Leu Tyr Thr Asn Thr Ser Arg Lys Ala Leu Glu
            340                 345                 350 gaa gtc agc ttg aag tgg att gac act gct tct aag ttc ggt aag ggt     1104
Glu Val Ser Leu Lys Trp Ile Asp Thr Ala Ser Lys Phe Gly Lys Gly
```

-continued

```
Glu Val Ser Leu Lys Trp Ile Asp Thr Ala Ser Lys Phe Gly Lys Gly
            355                 360                 365 aga ttc caa acc cca gct gaa aag cat gct ttc atg ggt act ttg aag    1152
Arg Phe Gln Thr Pro Ala Glu Lys His Ala Phe Met Gly Thr Leu Lys
    370                 375                 380 aag gac ttg taa                                                    1164
Lys Asp Leu
385

<210> SEQ ID NO 8
<211> LENGTH: 387
<212> TYPE: PRT
<213> ORGANISM: Saccharomyces cerevisiae

<400> SEQUENCE: 8

Met Ser His Arg Lys Tyr Glu Ala Pro Arg His Gly His Leu Gly Phe
  1               5                  10                  15

Leu Pro Arg Lys Arg Ala Ala Ser Ile Arg Ala Arg Val Lys Ala Phe
             20                  25                  30

Pro Lys Asp Asp Arg Ser Lys Pro Val Ala Leu Thr Ser Phe Leu Gly
         35                  40                  45

Tyr Lys Ala Gly Met Thr Thr Ile Val Arg Asp Leu Asp Arg Pro Gly
     50                  55                  60

Ser Lys Phe His Lys Arg Glu Val Val Glu Ala Val Thr Val Val Asp
 65                  70                  75                  80

Thr Pro Pro Val Val Val Gly Val Gly Tyr Val Glu Thr Pro
                 85                  90                  95

Arg Gly Leu Arg Ser Leu Thr Thr Val Trp Ala Glu His Leu Ser Asp
                100                 105                 110

Glu Val Lys Arg Arg Phe Tyr Lys Asn Trp Tyr Lys Ser Lys Lys Lys
            115                 120                 125

Ala Phe Thr Lys Tyr Ser Ala Lys Tyr Ala Gln Asp Gly Ala Gly Ile
        130                 135                 140

Glu Arg Glu Leu Ala Arg Ile Lys Lys Tyr Ala Ser Val Val Arg Val
145                 150                 155                 160

Leu Val His Thr Gln Ile Arg Lys Thr Pro Leu Ala Gln Lys Lys Ala
                165                 170                 175

His Leu Ala Glu Ile Gln Leu Asn Gly Gly Ser Ile Ser Glu Lys Val
            180                 185                 190

Asp Trp Ala Arg Glu His Phe Glu Lys Thr Val Ala Val Asp Ser Val
        195                 200                 205

Phe Glu Gln Asn Glu Met Ile Asp Ala Ile Ala Val Thr Lys Gly His
    210                 215                 220

Gly Phe Glu Gly Val Thr His Arg Trp Gly Thr Lys Lys Leu Pro Arg
225                 230                 235                 240

Lys Thr His Arg Gly Leu Arg Lys Val Ala Cys Ile Gly Ala Cys His
                245                 250                 255

Pro Ala His Val Met Trp Ser Val Ala Arg Ala Gly Gln Arg Gly Tyr
            260                 265                 270

His Ser Arg Thr Ser Ile Asn His Lys Ile Tyr Arg Val Gly Lys Gly
        275                 280                 285

Asp Asp Glu Ala Asn Gly Ala Thr Ser Phe Asp Arg Thr Lys Lys Thr
    290                 295                 300

Ile Thr Pro Met Gly Gly Phe Val His Tyr Gly Glu Ile Lys Asn Asp
305                 310                 315                 320
```

```
Phe Ile Met Val Lys Gly Cys Ile Pro Gly Asn Arg Lys Arg Ile Val
            325                 330                 335

Thr Leu Arg Lys Ser Leu Tyr Thr Asn Thr Ser Arg Lys Ala Leu Glu
            340                 345                 350

Glu Val Ser Leu Lys Trp Ile Asp Thr Ala Ser Lys Phe Gly Lys Gly
            355                 360                 365

Arg Phe Gln Thr Pro Ala Glu Lys His Ala Phe Met Gly Thr Leu Lys
            370                 375                 380

Lys Asp Leu
385

<210> SEQ ID NO 9
<211> LENGTH: 1164
<212> TYPE: DNA
<213> ORGANISM: Saccharomyces cerevisiae
<220> FEATURE:
<221> NAME/KEY: CDS
<222> LOCATION: (1)..(1161)

<400> SEQUENCE: 9 atg tct cac aga aag tac gaa gca cca cgt cac ggt cat tta ggt ttc      48
Met Ser His Arg Lys Tyr Glu Ala Pro Arg His Gly His Leu Gly Phe
  1               5                  10                  15 ttg cca aga aag aga gct gcc tcc atc aga gct aga gtt aag gct ttt      96
Leu Pro Arg Lys Arg Ala Ala Ser Ile Arg Ala Arg Val Lys Ala Phe
             20                  25                  30 cca aag gat gac aga tcc aag cca gtt gct cta act tcc ttc ttg ggt     144
Pro Lys Asp Asp Arg Ser Lys Pro Val Ala Leu Thr Ser Phe Leu Gly
         35                  40                  45 tac aag gct ggt atg acc acc att gtc aga gat ttg gac aga cca ggt     192
Tyr Lys Ala Gly Met Thr Thr Ile Val Arg Asp Leu Asp Arg Pro Gly
     50                  55                  60 tct aag ttc cac aag cgt gaa gtt gtc gaa gct gtc acc gtt gtt gac     240
Ser Lys Phe His Lys Arg Glu Val Val Glu Ala Val Thr Val Val Asp
 65                  70                  75                  80 act cca cca gtt gtc gtt gtt ggt gtt gtc ggt tac gtc gaa acc cca     288
Thr Pro Pro Val Val Val Val Gly Val Val Gly Tyr Val Glu Thr Pro
                 85                  90                  95 aga ggt ttg aga tct ttg acc acc gtc tgg gct gaa cat ttg tct gac     336
Arg Gly Leu Arg Ser Leu Thr Thr Val Trp Ala Glu His Leu Ser Asp
            100                 105                 110 gaa gtc aag aga aga ttc tac aag aac tgg tac aag tct aag aag aag     384
Glu Val Lys Arg Arg Phe Tyr Lys Asn Trp Tyr Lys Ser Lys Lys Lys
            115                 120                 125 gct ttc acc aaa tac tct gcc aag tac gct caa gat ggt gct ggt att     432
Ala Phe Thr Lys Tyr Ser Ala Lys Tyr Ala Gln Asp Gly Ala Gly Ile
        130                 135                 140 gaa aga gaa ttg gct aga atc aag aag tac gct tcc gtc gtc aga gtt     480
Glu Arg Glu Leu Ala Arg Ile Lys Lys Tyr Ala Ser Val Val Arg Val
145                 150                 155                 160 ttg gtc cac act caa atc aga aag act cca ttg gct caa aag aag gct     528
Leu Val His Thr Gln Ile Arg Lys Thr Pro Leu Ala Gln Lys Lys Ala
                165                 170                 175 cat ttg gct gaa atc caa ttg aac ggt ggt tcc atc tct gaa aag gtt     576
His Leu Ala Glu Ile Gln Leu Asn Gly Gly Ser Ile Ser Glu Lys Val
            180                 185                 190 gac tgg gct cgt gaa cat ttc gaa aag act gtt gct gtc gac agc gtt     624
Asp Trp Ala Arg Glu His Phe Glu Lys Thr Val Ala Val Asp Ser Val
            195                 200                 205 ttt gaa caa aac gaa atg att gac gct att gct gtc acc aag ggt cac     672
```

```
                                                           -continued

Phe Glu Gln Asn Glu Met Ile Asp Ala Ile Ala Val Thr Lys Gly His
    210                 215                 220 ggt ttc gaa ggt gtt acc cac aga tgg ggt act aag aaa ttg cca aga       720
Gly Phe Glu Gly Val Thr His Arg Trp Gly Thr Lys Lys Leu Pro Arg
225                 230                 235                 240 aag act cac aga ggt cta aga aag gtt gct tgt att ggt gct tgc cat       768
Lys Thr His Arg Gly Leu Arg Lys Val Ala Cys Ile Gly Ala Cys His
                245                 250                 255 tca gcc cac gtt atg tgg agt gtt gcc aga gct ggt caa aga ggt tac       816
Ser Ala His Val Met Trp Ser Val Ala Arg Ala Gly Gln Arg Gly Tyr
            260                 265                 270 cat tcc aga acc tcc att aac cac aag att tac aga gtc ggt aag ggt       864
His Ser Arg Thr Ser Ile Asn His Lys Ile Tyr Arg Val Gly Lys Gly
        275                 280                 285 gat gat gaa gct aac ggt gct acc agc ttc gac aga acc aag aag act       912
Asp Asp Glu Ala Asn Gly Ala Thr Ser Phe Asp Arg Thr Lys Lys Thr
    290                 295                 300 att acc cca atg ggt ggt ttc gtc cac tac ggt gaa att aag aac gac       960
Ile Thr Pro Met Gly Gly Phe Val His Tyr Gly Glu Ile Lys Asn Asp
305                 310                 315                 320 ttc atc atg gtt aaa ggt tgt atc cca ggt aac aga aag aga att gtt      1008
Phe Ile Met Val Lys Gly Cys Ile Pro Gly Asn Arg Lys Arg Ile Val
                325                 330                 335 act ttg aga aag tct ttg tac acc aac act tct aga aag gct ttg gaa      1056
Thr Leu Arg Lys Ser Leu Tyr Thr Asn Thr Ser Arg Lys Ala Leu Glu
            340                 345                 350 gaa gtc agc ttg aag tgg att gac act gct tct aag ttc ggt aag ggt      1104
Glu Val Ser Leu Lys Trp Ile Asp Thr Ala Ser Lys Phe Gly Lys Gly
        355                 360                 365 aga ttc caa acc cca gct gaa aag cat gct ttc atg ggt act ttg aag      1152
Arg Phe Gln Thr Pro Ala Glu Lys His Ala Phe Met Gly Thr Leu Lys
    370                 375                 380 aag gac ttg taa                                                      1164
Lys Asp Leu
385

<210> SEQ ID NO 10
<211> LENGTH: 387
<212> TYPE: PRT
<213> ORGANISM: Saccharomyces cerevisiae

<400> SEQUENCE: 10

Met Ser His Arg Lys Tyr Glu Ala Pro Arg His Gly His Leu Gly Phe
1               5                   10                  15

Leu Pro Arg Lys Arg Ala Ala Ser Ile Arg Ala Arg Val Lys Ala Phe
                20                  25                  30

Pro Lys Asp Asp Arg Ser Lys Pro Val Ala Leu Thr Ser Phe Leu Gly
            35                  40                  45

Tyr Lys Ala Gly Met Thr Thr Ile Val Arg Asp Leu Asp Arg Pro Gly
        50                  55                  60

Ser Lys Phe His Lys Arg Glu Val Val Glu Ala Val Thr Val Val Asp
65                  70                  75                  80

Thr Pro Pro Val Val Val Gly Val Gly Tyr Val Glu Thr Pro
                85                  90                  95

Arg Gly Leu Arg Ser Leu Thr Thr Val Trp Ala Glu His Leu Ser Asp
            100                 105                 110

Glu Val Lys Arg Arg Phe Tyr Lys Asn Trp Tyr Lys Ser Lys Lys Lys
        115                 120                 125
```

-continued

```
Ala Phe Thr Lys Tyr Ser Ala Lys Tyr Ala Gln Asp Gly Ala Gly Ile
    130                 135                 140
Glu Arg Glu Leu Ala Arg Ile Lys Lys Tyr Ala Ser Val Val Arg Val
145                 150                 155                 160
Leu Val His Thr Gln Ile Arg Lys Thr Pro Leu Ala Gln Lys Lys Ala
                165                 170                 175
His Leu Ala Glu Ile Gln Leu Asn Gly Gly Ser Ile Ser Glu Lys Val
            180                 185                 190
Asp Trp Ala Arg Glu His Phe Glu Lys Thr Val Ala Val Asp Ser Val
        195                 200                 205
Phe Glu Gln Asn Glu Met Ile Asp Ala Ile Ala Val Thr Lys Gly His
    210                 215                 220
Gly Phe Glu Gly Val Thr His Arg Trp Gly Thr Lys Lys Leu Pro Arg
225                 230                 235                 240
Lys Thr His Arg Gly Leu Arg Lys Val Ala Cys Ile Gly Ala Cys His
                245                 250                 255
Ser Ala His Val Met Trp Ser Val Ala Arg Ala Gly Gln Arg Gly Tyr
            260                 265                 270
His Ser Arg Thr Ser Ile Asn His Lys Ile Tyr Arg Val Gly Lys Gly
        275                 280                 285
Asp Asp Glu Ala Asn Gly Ala Thr Ser Phe Asp Arg Thr Lys Lys Thr
    290                 295                 300
Ile Thr Pro Met Gly Gly Phe Val His Tyr Gly Glu Ile Lys Asn Asp
305                 310                 315                 320
Phe Ile Met Val Lys Gly Cys Ile Pro Gly Asn Arg Lys Arg Ile Val
                325                 330                 335
Thr Leu Arg Lys Ser Leu Tyr Thr Asn Thr Ser Arg Lys Ala Leu Glu
            340                 345                 350
Glu Val Ser Leu Lys Trp Ile Asp Thr Ala Ser Lys Phe Gly Lys Gly
        355                 360                 365
Arg Phe Gln Thr Pro Ala Glu Lys His Ala Phe Met Gly Thr Leu Lys
    370                 375                 380
Lys Asp Leu
385

<210> SEQ ID NO 11
<211> LENGTH: 1164
<212> TYPE: DNA
<213> ORGANISM: Saccharomyces cerevisiae
<220> FEATURE:
<221> NAME/KEY: CDS
<222> LOCATION: (1)..(1161)

<400> SEQUENCE: 11 atg tct cac aga aag tac gaa gca cca cgt cac ggt cat tta ggt ttc      48
Met Ser His Arg Lys Tyr Glu Ala Pro Arg His Gly His Leu Gly Phe
1               5                   10                  15 ttg cca aga aag aga gct gcc tcc atc aga gct aga gtt aag gct ttt      96
Leu Pro Arg Lys Arg Ala Ala Ser Ile Arg Ala Arg Val Lys Ala Phe
            20                  25                  30 cca aag gat gac aga tcc aag cca gtt gct cta act tcc ttc ttg ggt     144
Pro Lys Asp Asp Arg Ser Lys Pro Val Ala Leu Thr Ser Phe Leu Gly
        35                  40                  45 tac aag gct ggt atg acc acc att gtc aga gat ttg gac aga cca ggt     192
Tyr Lys Ala Gly Met Thr Thr Ile Val Arg Asp Leu Asp Arg Pro Gly
    50                  55                  60 tct aag ttc cac aag cgt gaa gtt gtc gaa gct gtc acc gtt gtt gac     240
```

```
Ser Lys Phe His Lys Arg Glu Val Val Glu Ala Val Thr Val Val Asp
 65                  70                  75                  80 act cca cca gtt gtc gtt gtt ggt gtt gtc ggt tac gtc gaa acc cca      288
Thr Pro Pro Val Val Val Val Gly Val Val Gly Tyr Val Glu Thr Pro
                 85                  90                  95 aga ggt ttg aga tct ttg acc acc gtc tgg gct gaa cat ttg tct gac      336
Arg Gly Leu Arg Ser Leu Thr Thr Val Trp Ala Glu His Leu Ser Asp
            100                 105                 110 gaa gtc aag aga aga ttc tac aag aac tgg tac aag tct aag aag aag      384
Glu Val Lys Arg Arg Phe Tyr Lys Asn Trp Tyr Lys Ser Lys Lys Lys
        115                 120                 125 gct ttc acc aaa tac tct gcc aag tac gct caa gat ggt gct ggt att      432
Ala Phe Thr Lys Tyr Ser Ala Lys Tyr Ala Gln Asp Gly Ala Gly Ile
    130                 135                 140 gaa aga gaa ttg gct aga atc aag aag tac gct tcc gtc gtc aga gtt      480
Glu Arg Glu Leu Ala Arg Ile Lys Lys Tyr Ala Ser Val Val Arg Val
145                 150                 155                 160 ttg gtc cac act caa atc aga aag act cca ttg gct caa aag aag gct      528
Leu Val His Thr Gln Ile Arg Lys Thr Pro Leu Ala Gln Lys Lys Ala
                165                 170                 175 cat ttg gct gaa atc caa ttg aac ggt ggt tcc atc tct gaa aag gtt      576
His Leu Ala Glu Ile Gln Leu Asn Gly Gly Ser Ile Ser Glu Lys Val
            180                 185                 190 gac tgg gct cgt gaa cat ttc gaa aag act gtt gct gtc gac agc gtt      624
Asp Trp Ala Arg Glu His Phe Glu Lys Thr Val Ala Val Asp Ser Val
        195                 200                 205 ttt gaa caa aac gaa atg att gac gct att gct gtc acc aag ggt cac      672
Phe Glu Gln Asn Glu Met Ile Asp Ala Ile Ala Val Thr Lys Gly His
    210                 215                 220 ggt ttc gaa ggt gtt acc cac aga tgg ggt act aag aaa ttg cca aga      720
Gly Phe Glu Gly Val Thr His Arg Trp Gly Thr Lys Lys Leu Pro Arg
225                 230                 235                 240 aag act cac aga ggt cta aga aag gtt gct tgt att ggt gct tgg cat      768
Lys Thr His Arg Gly Leu Arg Lys Val Ala Cys Ile Gly Ala Trp His
                245                 250                 255 cca gcc cac gtt atg tgg agt gtt gcc aga gct ggt caa aga ggt tac      816
Pro Ala His Val Met Trp Ser Val Ala Arg Ala Gly Gln Arg Gly Tyr
            260                 265                 270 cat tcc aga acc tcc att aac cac aag act tac aga gtc ggt aag ggt      864
His Ser Arg Thr Ser Ile Asn His Lys Thr Tyr Arg Val Gly Lys Gly
        275                 280                 285 gat gat gaa gct aac ggt gct acc agc ttc gac aga acc aag aag act      912
Asp Asp Glu Ala Asn Gly Ala Thr Ser Phe Asp Arg Thr Lys Lys Thr
    290                 295                 300 att acc cca atg ggt ggt ttc gtc cac tac ggt gaa att aag aac gac      960
Ile Thr Pro Met Gly Gly Phe Val His Tyr Gly Glu Ile Lys Asn Asp
305                 310                 315                 320 ttc atc atg gtt aaa ggt tgt atc cca ggt aac aga aag aga att gtt     1008
Phe Ile Met Val Lys Gly Cys Ile Pro Gly Asn Arg Lys Arg Ile Val
                325                 330                 335 act ttg aga aag tct ttg tac acc aac act tct aga aag gct ttg gaa     1056
Thr Leu Arg Lys Ser Leu Tyr Thr Asn Thr Ser Arg Lys Ala Leu Glu
            340                 345                 350 gaa gtc agc ttg aag tgg att gac act gct tct aag ttc ggt aag ggt     1104
Glu Val Ser Leu Lys Trp Ile Asp Thr Ala Ser Lys Phe Gly Lys Gly
        355                 360                 365 aga ttc caa acc cca gct gaa aag cat gct ttc atg ggt act ttg aag     1152
Arg Phe Gln Thr Pro Ala Glu Lys His Ala Phe Met Gly Thr Leu Lys
    370                 375                 380
```

```
aag gac ttg taa                                                              1164
Lys Asp Leu
385
```

<210> SEQ ID NO 12
<211> LENGTH: 387
<212> TYPE: PRT
<213> ORGANISM: Saccharomyces cerevisiae

<400> SEQUENCE: 12

```
Met Ser His Arg Lys Tyr Glu Ala Pro Arg His Gly His Leu Gly Phe
1               5                  10                  15

Leu Pro Arg Lys Arg Ala Ala Ser Ile Arg Ala Arg Val Lys Ala Phe
            20                  25                  30

Pro Lys Asp Asp Arg Ser Lys Pro Val Ala Leu Thr Ser Phe Leu Gly
        35                  40                  45

Tyr Lys Ala Gly Met Thr Thr Ile Val Arg Asp Leu Asp Arg Pro Gly
    50                  55                  60

Ser Lys Phe His Lys Arg Glu Val Val Glu Ala Val Thr Val Val Asp
65                  70                  75                  80

Thr Pro Pro Val Val Val Gly Val Val Gly Tyr Val Glu Thr Pro
                85                  90                  95

Arg Gly Leu Arg Ser Leu Thr Thr Val Trp Ala Glu His Leu Ser Asp
            100                 105                 110

Glu Val Lys Arg Arg Phe Tyr Lys Asn Trp Tyr Lys Ser Lys Lys Lys
        115                 120                 125

Ala Phe Thr Lys Tyr Ser Ala Lys Tyr Ala Gln Asp Gly Ala Gly Ile
    130                 135                 140

Glu Arg Glu Leu Ala Arg Ile Lys Lys Tyr Ala Ser Val Val Arg Val
145                 150                 155                 160

Leu Val His Thr Gln Ile Arg Lys Thr Pro Leu Ala Gln Lys Lys Ala
                165                 170                 175

His Leu Ala Glu Ile Gln Leu Asn Gly Gly Ser Ile Ser Glu Lys Val
            180                 185                 190

Asp Trp Ala Arg Glu His Phe Glu Lys Thr Val Ala Val Asp Ser Val
        195                 200                 205

Phe Glu Gln Asn Glu Met Ile Asp Ala Ile Ala Val Thr Lys Gly His
    210                 215                 220

Gly Phe Glu Gly Val Thr His Arg Trp Gly Thr Lys Lys Leu Pro Arg
225                 230                 235                 240

Lys Thr His Arg Gly Leu Arg Lys Val Ala Cys Ile Gly Ala Trp His
                245                 250                 255

Pro Ala His Val Met Trp Ser Val Ala Arg Ala Gly Gln Arg Gly Tyr
            260                 265                 270

His Ser Arg Thr Ser Ile Asn His Lys Thr Tyr Arg Val Gly Lys Gly
        275                 280                 285

Asp Asp Glu Ala Asn Gly Ala Thr Ser Phe Asp Arg Thr Lys Lys Thr
    290                 295                 300

Ile Thr Pro Met Gly Gly Phe Val His Tyr Gly Glu Ile Lys Asn Asp
305                 310                 315                 320

Phe Ile Met Val Lys Gly Cys Ile Pro Gly Asn Arg Lys Arg Ile Val
                325                 330                 335

Thr Leu Arg Lys Ser Leu Tyr Thr Asn Thr Ser Arg Lys Ala Leu Glu
            340                 345                 350

Glu Val Ser Leu Lys Trp Ile Asp Thr Ala Ser Lys Phe Gly Lys Gly
```

-continued

```
                     355                 360                 365
Arg Phe Gln Thr Pro Ala Glu Lys His Ala Phe Met Gly Thr Leu Lys
        370                 375                 380

Lys Asp Leu
385

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 13
ccccggtacc tcacgcacac tggaatgaat                                      30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 14
ccccgagcgc aacctccatt ttggacttgg                                      30
```